US009480847B2

(12) United States Patent
Greene et al.

(10) Patent No.: US 9,480,847 B2
(45) Date of Patent: Nov. 1, 2016

(54) OPTIMIZING DATA RETRIEVAL FROM AN ACTIVE IMPLANTABLE MEDICAL DEVICE

(71) Applicant: NeuroPace, Inc., Mountain View, CA (US)

(72) Inventors: David A. Greene, Fort Wayne, IN (US); Steve T. Archer, Sunnyvale, CA (US); Patrick G. Mulligan, IV, Belmont, CA (US)

(73) Assignee: NeuroPace, Inc., Mountain View, CA (US)

(*) Notice: Subject to any disclaimer, the term of this patent is extended or adjusted under 35 U.S.C. 154(b) by 0 days.

(21) Appl. No.: 14/955,960

(22) Filed: Dec. 1, 2015

(65) Prior Publication Data

US 2016/0089544 A1 Mar. 31, 2016

Related U.S. Application Data

(62) Division of application No. 13/830,021, filed on Mar. 14, 2013, now Pat. No. 9,238,144.

(51) Int. Cl.
*A61N 1/372* (2006.01)
*H04Q 5/22* (2006.01)
*H04R 25/00* (2006.01)
*H04B 7/00* (2006.01)

(52) U.S. Cl.
CPC ....... *A61N 1/37252* (2013.01); *A61N 1/37276* (2013.01)

(58) Field of Classification Search
CPC ........ A61N 1/372; H04Q 5/22; H04R 25/00; H04B 7/00; H04W 36/00
USPC ................. 340/10.1–10.5, 505, 539, 572.1; 455/522, 524, 442; 381/312, 315
See application file for complete search history.

(56) References Cited

U.S. PATENT DOCUMENTS

| | | | |
|---|---|---|---|
| 5,992,223 A | 11/1999 | Sabins et al. | |
| 6,331,160 B1 | 12/2001 | Bardy | |
| 6,563,417 B1 | 5/2003 | Shaw | |
| 6,718,197 B1 | 4/2004 | Carlson et al. | |
| 6,839,447 B2* | 1/2005 | Nielsen | H04R 25/554 381/312 |
| 7,581,075 B1 | 8/2009 | Ciot | |
| 7,801,620 B2 | 9/2010 | Freeberg | |
| 7,925,356 B2* | 4/2011 | Li | A61N 1/37223 128/903 |
| 7,949,388 B1 | 5/2011 | Fong | |
| 8,189,832 B2* | 5/2012 | Boguslavskij | H04W 52/24 381/312 |
| 8,200,270 B2* | 6/2012 | Ariyur | H04W 52/241 455/442 |
| 8,204,593 B2 | 6/2012 | Sheldon et al. | |
| 8,386,043 B2 | 2/2013 | Bange et al. | |
| 8,458,059 B2 | 6/2013 | Crane | |
| 8,517,941 B1 | 8/2013 | Wenzel | |
| 8,540,644 B2 | 9/2013 | Husheer | |
| 8,812,127 B2 | 8/2014 | Freeberg | |
| 8,868,185 B2 | 10/2014 | Zielinski et al. | |

(Continued)

*Primary Examiner* — Nam V Nguyen
(74) *Attorney, Agent, or Firm* — Loza & Loza, LLP; David S. Sarisky

(57) ABSTRACT

An external data retrieval apparatus includes a transceiver, and a processing system coupled to the transceiver. The processing system obtains a plurality of measures over a period of time. The measures relate to a quality of a communications channel between the data retrieval apparatus and an active implantable medical device. The processing system determines a trend in the plurality of measures over the period of time, and then determines a preferred time during which to retrieve data based on the trend.

16 Claims, 14 Drawing Sheets

(56) References Cited

U.S. PATENT DOCUMENTS

| | | | |
|---|---|---|---|
| 9,148,736 B2* | 9/2015 | Fort | H04R 25/505 |
| 9,232,485 B2* | 1/2016 | Wu | |
| 9,259,582 B2* | 2/2016 | Joshi | A61N 1/37229 |
| 9,270,134 B2* | 2/2016 | Gaddam | H02J 7/007 |
| 9,289,614 B2* | 3/2016 | Wu | A61N 1/37252 |
| 2011/0208261 A1 | 8/2011 | Levine et al. | |

* cited by examiner

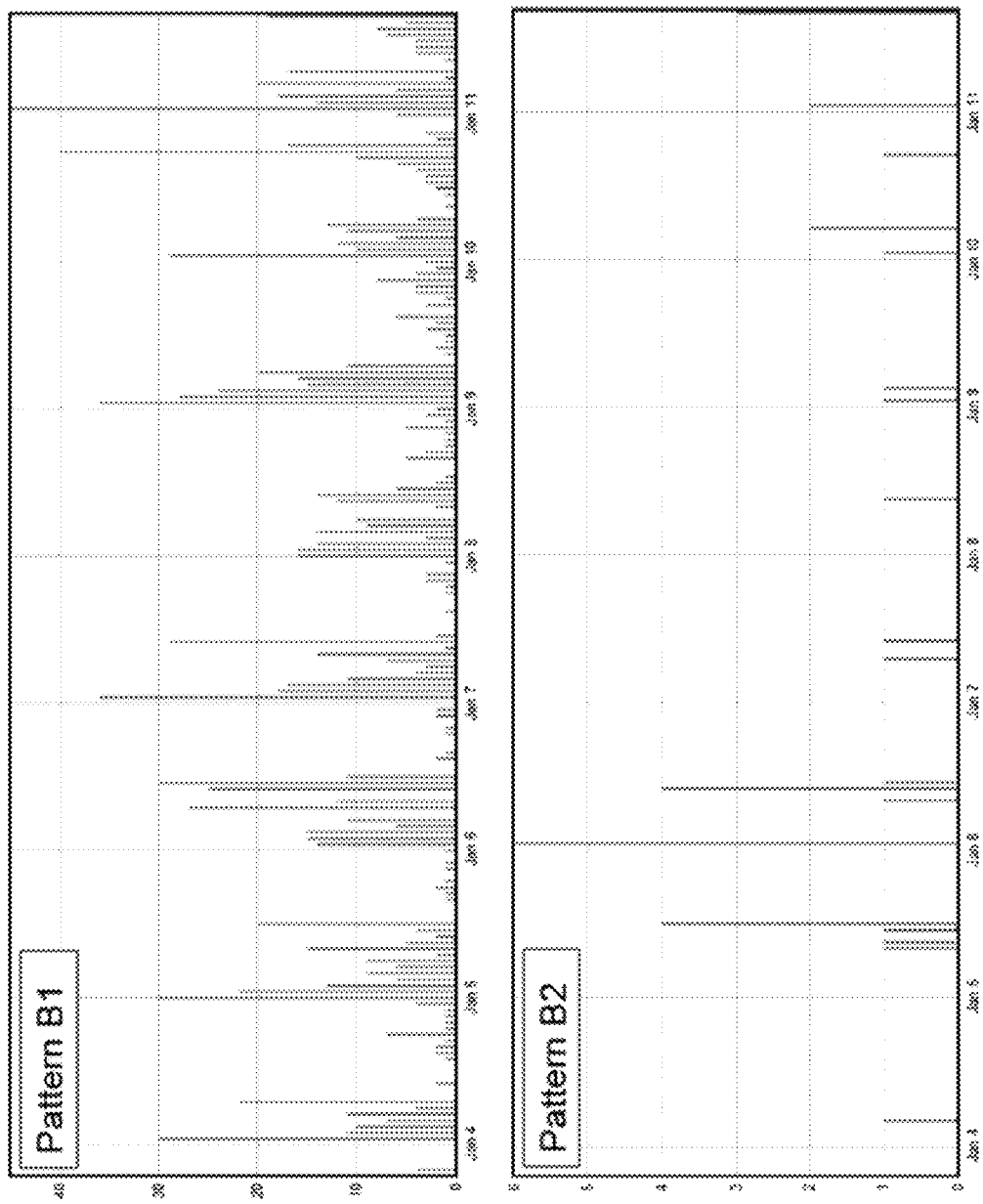

FIG. 13

| | 8:00 | 9:00 | 10:00 | 11:00 | 12:00 | 13:00 | 14:00 | 15:00 | 16:00 | 17:00 | 18:00 | 19:00 | 20:00 | 21:00 | 22:00 | 23:00 | 0:00 | 1:00 | 2:00 | 3:00 | 4:00 | 5:00 | 6:00 | 7:00 |
|---|---|---|---|---|---|---|---|---|---|---|---|---|---|---|---|---|---|---|---|---|---|---|---|---|
| Day 1 | 0 | 0 | 0 | 0 | 0 | 3 | 0 | 0 | 0 | 1 | 0 | 0 | 0 | 4 | 4 | 4 | 4 | 4 | 4 | 4 | 4 | 4 | 0 | 0 |
| Day 2 | 0 | 0 | 0 | 1 | 0 | 0 | 0 | 0 | 0 | 0 | 0 | 0 | 0 | 4 | 4 | 4 | 4 | 4 | 4 | 4 | 4 | 4 | 0 | 0 |
| Day 3 | 0 | 1 | 0 | 0 | 0 | 1 | 0 | 0 | 0 | 0 | 0 | 1 | 4 | 4 | 4 | 4 | 4 | 4 | 4 | 4 | 4 | 4 | 0 | 0 |
| Day 4 | 0 | 0 | 0 | 0 | 1 | 1 | 2 | 0 | 0 | 0 | 0 | 0 | 0 | 0 | 0 | 4 | 4 | 4 | 4 | 4 | 4 | 4 | 0 | 0 |
| Day 5 | 0 | 1 | 0 | 0 | 0 | 0 | 0 | 0 | 0 | 0 | 0 | 0 | 1 | 0 | 4 | 4 | 4 | 4 | 4 | 4 | 4 | 4 | 0 | 0 |
| Day 6 | 0 | 0 | 0 | 0 | 0 | 0 | 0 | 4 | 0 | 0 | 0 | 0 | 0 | 0 | 4 | 4 | 4 | 4 | 4 | 4 | 4 | 4 | 0 | 0 |
| Day 7 | 0 | 0 | 0 | 0 | 0 | 0 | 0 | 1 | 0 | 1 | 0 | 1 | 0 | 0 | 1 | 0 | 4 | 4 | 4 | 4 | 4 | 4 | 0 | 0 |
| Average | 0.0 | 0.3 | 0.0 | 0.1 | 0.1 | 0.7 | 0.3 | 0.7 | 0.0 | 0.3 | 0.0 | 0.3 | 1.3 | 1.7 | 3.0 | 3.4 | 4.0 | 4.0 | 4.0 | 4.0 | 4.0 | 4.0 | 0.0 | 0.0 |

Time of Day

OPTIMIZING DATA RETRIEVAL FROM AN ACTIVE IMPLANTABLE MEDICAL DEVICE

CROSS-REFERENCE TO RELATED APPLICATION(S)

This application is a divisional of U.S. application Ser. No. 13/830,021, entitled "Optimizing Data Retrieval From an Active Implantable Medical Device" and filed on Mar. 14, 2013, now U.S. Pat. No. 9,238,144, which is expressly incorporated by reference herein in its entirety.

BACKGROUND

1. Field

The present disclosure relates generally to wireless communications involving active implantable medical devices, and more particularly, to apparatuses and methods for optimizing the retrieval of data from active implantable medical devices.

2. Background

Modern active implantable medical devices, such as neurostimulators, pacemakers, and ICDs, are capable of not only monitoring patient condition and delivering therapy, but are capable of storing detailed data and diagnostics relating to a patient's condition for later retrieval. Analysis of this data can improve patient care dramatically, and allow fine-tuning the performance of the implantable devices by programming them with new operational parameters. Interrogation of an implantable medical device allows data stored in the device to be retrieved by an external device. After analysis, reprogramming the device allows its performance to be optimized based on the interrogated data.

An active implantable medical device can store data, for later retrieval, that are useful for assessment of the patient's medical status and for determining the operational status of the implantable medical device. Retrieval of such data, however, requires establishment of communications links between the implantable medical device and an external device. Such communications may consume significant implantable medical device energy, which may reduce the longevity of the implantable medical device. Furthermore, an implantable medical device has limited memory for storing patient data. As such, infrequent retrieval of patent data from an implantable medical device may cause the implantable medical device to stop storing data, or to overwrite older data in order to store new data.

It would be desirable to provide mechanisms that optimize the retrieval of patient data in a manner that reduces implantable medical device energy consumption and prevents loss of stored patient data. The concepts disclosed below address these needs and others.

SUMMARY

In one aspect of the disclosure, a method of, and apparatus for, data retrieval by an external data retrieval apparatus are provided. The method involves obtaining a number of measures over a period of time. The measures correspond to a quality of a communications channel between the data retrieval apparatus and an active implantable medical device. The method also includes determining a trend in the number of measures over the period of time. The trends may represent changes in the measures as a function of time. The further includes determining a preferred time during which to retrieve data based on the trend. For example, the time may be the time in the trend at which the quality measure is at a peak, or a time range during which the quality measure exceeds a minimum quality threshold. The apparatus includes a transceiver and a processing system. The processing system is coupled to the transceiver and includes various modules configured to perform the described method.

Thus, in this aspect of the disclosure, a data retrieval apparatus queries an active implantable medical device systematically to assess the time periods when the signal strength at the data retrieval apparatus is maximal for extended periods of time. The method involves periodic, brief communications between the data retrieval apparatus and the active implantable medical device to determine when the active implantable medical device is in close proximity to the data retrieval apparatus. Further optimizations determine the central periods of time when the active implantable medical device is most likely to be in close proximity to maximize the probability of energy transfer using the least active implantable medical device battery energy possible.

In another aspect of the disclosure, a method of, and apparatus for, power transmission control by an active implantable medical device are provided. The method involves receiving a measure of quality of a signal transmitted by the active implantable medical device. The measure is received from an external data retrieval apparatus that received the signal transmitted by the active implantable medical device. The method also includes comparing the measure to a criterion. The criterion may correspond to a minimum quality measure, which in turn, corresponds to a minimum performance requirement, e.g., data rate, for a communication channel between the active implantable medical device and the data retrieval apparatus. The measure of quality may be one of a signal-to-noise ratio, a received signal strength indicator, or a packet error rate. The method further involves adjusting a signal transmission power level of the active implantable medical device until the measure is at or near the criterion. The apparatus includes a transceiver and a processing system. The processing system is coupled to the transceiver and includes various modules configured to perform the described method.

Thus, in this aspect of the disclosure, an active implantable medical device uses a feedback signal from a data retrieval apparatus to adjust the level of RF transmission power by the active implantable medical device to produce the minimum signal strength at the data retrieval apparatus needed to reliably support quality communication between the active implantable medical device and the data retrieval apparatus.

In another aspect of the disclosure, a method of, and apparatus for, data retrieval by an external data retrieval apparatus are provided. The method involves retrieving different data types from active implantable medical device, where each data type has a portion of a memory of the active implantable medical device allocated thereto. The method also involves, for each of the different data types, scheduling a next retrieval of the data type based on a known period of time or based on time data included in retrieved data. The data type may be a first type that corresponds to a count of a number of occurrences of at least one type of a physiological event over a period of time. In this case, the time until the next scheduled retrieval of the first type is a percentage of the period of time. The data type may be a second type that corresponds to a time of occurrence of each of a plurality of physiological events, in order of occurrence. In this case, the time until the next scheduled retrieval of the second type is a percentage of elapsed time between the oldest occurrence and the most recent occurrence. The data type may be a third type that corresponds to one or more waveforms of one or more physiological events. In this case, the time until the next scheduled retrieval of the third type is a percentage of the time elapsed since the occurrence of the oldest waveform. The method may also include setting a limit on the amount of data to be retrieved during a period of time. In this case, the data retrieval schedule thus described is subordinate to the limit. The apparatus includes a transceiver and a processing system. The processing system is coupled to the transceiver and includes various modules configured to perform the described method.

Thus, in this aspect of the disclosure, adaptive interrogation intervals are implemented by a data retrieval apparatus. The adaptation recognizes several data types present in an active implantable medical device that have differing time intervals prior to overwrite. The disclosed method assesses when retrieval should occur on a differential basis based on the data type so that data overwrite does not occur for any data type, while avoiding too frequent data transfer for any data type that could increase energy usage by the active implantable medical device. The adaptation also accounts for incorporation of programmable constraints that limit total data retrieval to avoid active implantable medical device battery depletion. Such constraints may be on a per-time basis or on a total data per time basis.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein:

FIG. 8B are illustrations of histogram data collected by an implantable medical device;

FIG. 13 is an illustration of a table of individual and average communication quality measurements over a seven day period.

DETAILED DESCRIPTION

Figure 1:
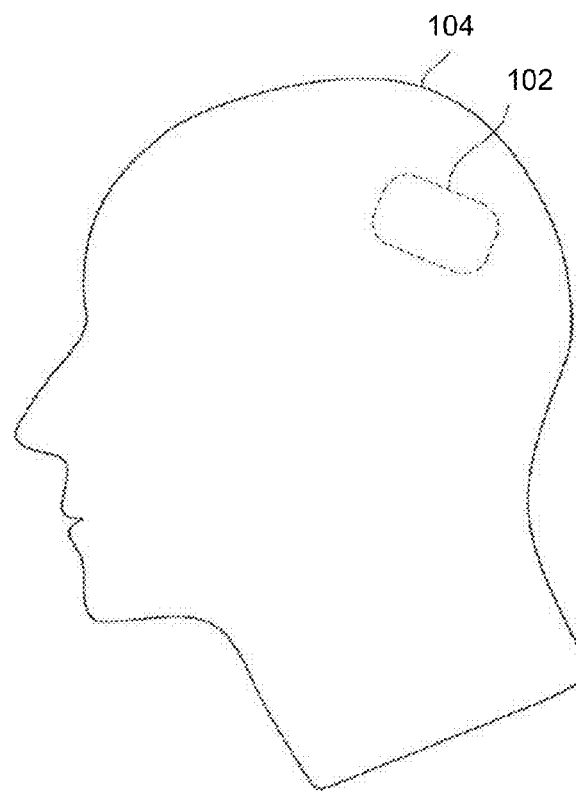
FIG. 1 is a schematic illustration of a patient's head showing the placement of an implantable medical device.

Various aspects of the disclosure will be described more fully hereinafter with reference to the accompanying drawings. This disclosure may, however, be embodied in many different forms by those skilled in the art and should not be construed as limited to any specific structure or function presented herein. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of this disclosure, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure and/or functionality in addition to or instead of other aspects of this disclosure. It should be understood that any aspect of the disclosure disclosed herein may be embodied by one or more elements of a claim.

The concepts disclosed may be implemented in hardware or software that is executed on a hardware platform. The hardware or hardware platform may be a general purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium. A computer-readable medium may include, by way of example, a magnetic storage device (e.g., hard disk, floppy disk, magnetic strip), an optical disk (e.g., compact disk (CD), digital versatile disk (DVD)), a smart card, a flash memory device (e.g., card, stick, key drive), random access memory (RAM), read only memory (ROM), programmable ROM (PROM), erasable PROM (EPROM), electrically erasable PROM (EEPROM), a general register, or any other suitable non-transitory medium for storing software.

As mention above, an implantable medical device (IMD) such as a pacemaker, implantable defibrillator, or neurostimulator stores data that are useful for assessing patient medical status and for determining the operational status of the implantable medical device. However, the amount of memory present in the implantable medical device is limited, so eventually the implantable medical device may stop storing data, or may need to overwrite older data to store new data. The term "overwrite" is used herein to describe data loss resulting from limited memory. To avoid overwrite, it is desirable to have a home appliance that can retrieve data from the implantable medical device between office visits in the patient's home. Such a home appliance, hereafter referred to as a data retrieval apparatus (DRA), would ideally use radio frequency (RF) telemetry to retrieve data transcutaneously from the implantable medical device when the patient is in close proximity. The data retrieval apparatus could be a standalone device that the patient would bring to their physician for read-out, or it could be internet connected to a central database. Ideally the data retrieval apparatus would have a telemetry range long enough for it to be placed in a convenient location where it could establish the telemetry link on a periodic basis without patient intervention. The methods and apparatuses described herein (1) automate the setup process of the data retrieval apparatus for both the patient and physician, (2) avoid data overwrite, and (3) minimize the energy consumed by the implantable medical device when transmitting data to the data retrieval apparatus. Automation of the setup process reduces physician workload. Avoiding data overwrite improves patient assessment and care. Reducing energy consumed by the implantable medical device during data transmission increases the life of the implantable medical device's battery and reduces the frequency of implantable medical device replacement surgical procedures, which in turn lowers surgical complications and reduces total medical costs.

With reference to FIG. 1, an exemplary implantable medical device 102 is shown implanted in a patient 104. In one configuration, the implantable medical device 102 includes a small self-contained brainwave detecting device. As the term is used herein, a brainwave detecting or recording device is a device capable of detecting or predicting ictal activity (or other neurological events) for providing data useful in the diagnosis of a neurological disorder. Further, the term recording device, as used herein, is a device that can either record neurological signals, such as EEG signals, or detect and analyze EEG signals and create a log of such an analysis.

The implantable medical device 102 may be configured to detect or predict neurological events that have a representative electrographic signature. For example, the implantable medical device 102 may be responsive to epileptic seizures. It should, however, be recognized that it is also possible to respond to other types of neurological disorders, such as movement disorders (e.g. the tremors characterizing Parkinson's disease), migraine headaches, chronic pain, and neuropsychiatric disorders such as depression.

Figure 2:
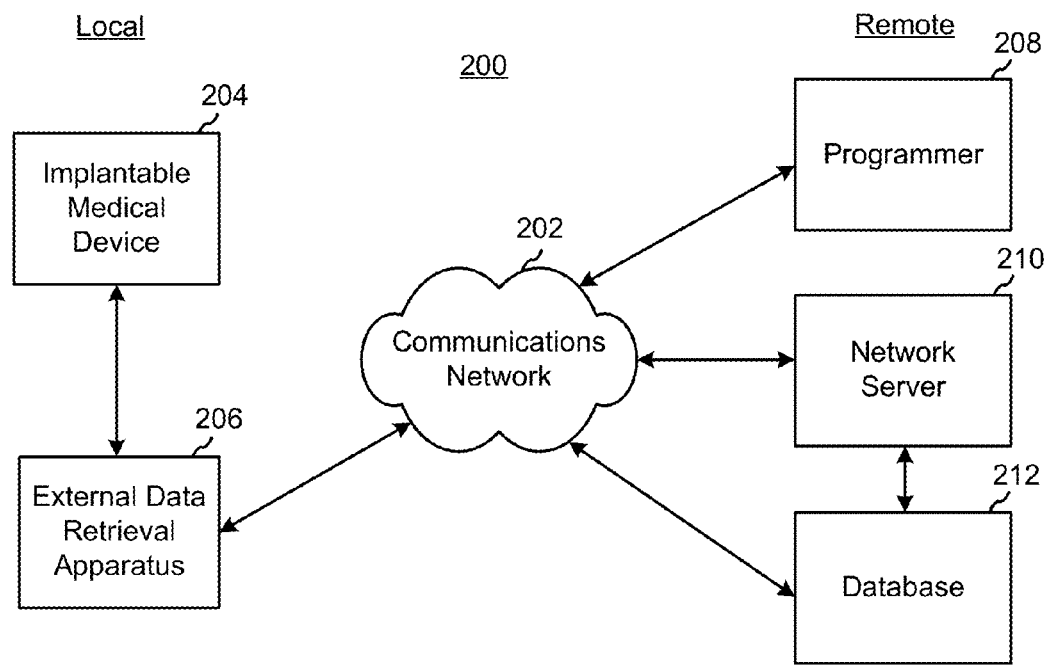
FIG. 2 is a block diagram of a system for providing communication between local medical devices and remote system components.

With reference to FIG. 2, an exemplary patient monitoring system 200 is illustrated. The patient monitoring system 200 includes local components and remote components that communicate through a communications network 202, such as the Internet. Local components are located in the vicinity of the patient, such as the patient's residence, and may include an implantable medical device 204, and a local device 206, referred to herein as a data retrieval apparatus. Remote components are located a significant distance from the patient, such as at a hospital or care provider's office. Remote components may include, for example, a programmer 208, a network server 210 and a database 212.

The programmer 208 is typically operated by medical personnel (such as the patient's treating physician) to control the operation of the implantable medical device 204. In general terms, the programmer 208 functions as a clinical interface to the implantable medical device 204, allowing the implantable medical device parameters to be modified, and for data and/or program code to be uploaded from and downloaded to the implantable medical device.

The database 212 serves as a centralized data repository for all data relevant to the operation of the system 200, and may include clinical data, program code, and more. The network server 210 acts as the primary interface between the database 212 and other devices attached to the communications network 202. Although it might be possible and advantageous in certain circumstances to communicate directly with the database 212, it is generally preferable to configure the network server 210 to receive queries, perform necessary authentication, access the database 212, and respond as necessary, thereby reducing the processing load on the database and also reducing the exposure of the database to network traffic (thereby improving security).

The data retrieval apparatus 206 is configured to receive data from remote components through the communications network 202 and provide it to the implantable medical device 204. Such data may include, for example, program code or instructions from a programmer 208 that affect the operation of the implantable medical device 204. The data retrieval apparatus 206 is also configured to retrieve data from the implantable medical device 204 and to forward it to one or more of the remote components. As described further below, communication between the data retrieval apparatus 202 and the implantable medical device 204 is wireless, and may be in the form of short-range telemetry by inductive coupling or long-range telemetry by RF communications.

Figure 3:
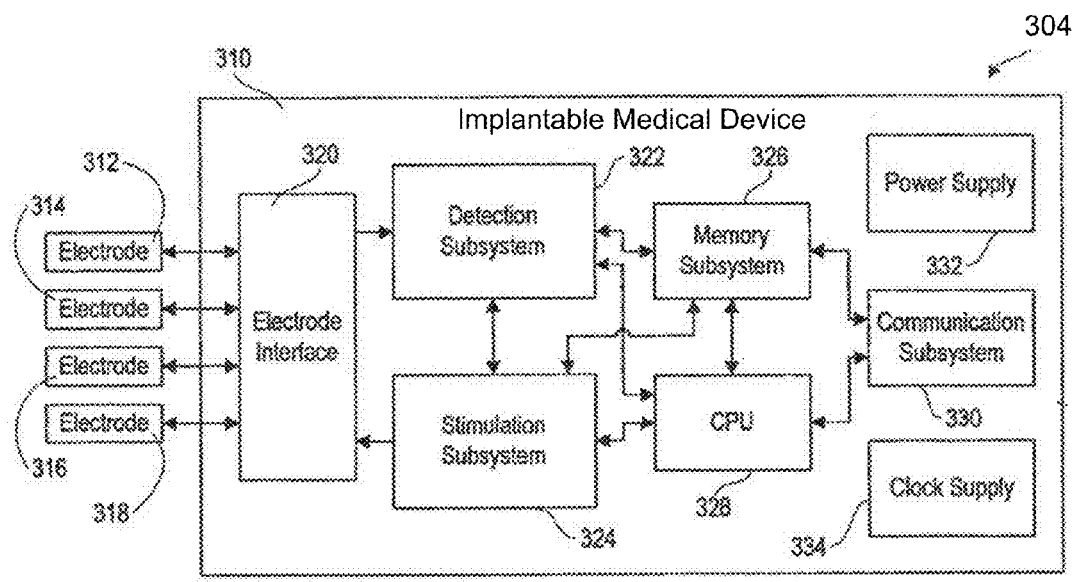
FIG. 3 is a block diagram of an implantable medical device.

An overall block diagram of an implantable medical device 304 used for measurement, detection, and treatment is illustrated in FIG. 3. Inside the housing of the device 304 are several subsystems making up a control module 310. The control module 310 is capable of being coupled to a plurality of electrodes 312, 314, 316, and 318 for sensing and stimulation. Although four electrodes are shown in FIG. 3, it should be recognized that any number is possible.

The electrodes 312-318 are connected to an electrode interface 320. Preferably, the electrode interface is capable of selecting each electrode as required for sensing and stimulation; accordingly the electrode interface is coupled to a detection subsystem 322 and a stimulation subsystem 324. The electrode interface also may provide any other features, capabilities, or aspects, including but not limited to amplification, isolation, and charge-balancing functions, that are required for a proper interface with neurological tissue and not provided by any other subsystem of the implantable medical device 304.

The detection subsystem 322 includes an EEG analyzer function. The EEG analyzer function is adapted to receive EEG signals from the electrodes 312-318, through the electrode interface 320, and to process those EEG signals to identify neurological activity indicative of a seizure, an onset of a seizure, or a precursor to a seizure. One way to implement such EEG analysis functionality is disclosed in detail in U.S. Pat. No. 6,016,449 to Fischell et al., which is hereby incorporated by reference. The detection subsystem may optionally also contain further sensing and detection capabilities, including but not limited to parameters derived from other physiological conditions (such as electrophysiological parameters, temperature, blood pressure, etc.).

The stimulation subsystem 324 is capable of applying electrical stimulation to neurological tissue through the electrodes 312-318. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 322. As illustrated in FIG. 3, the stimulation subsystem 324 and the EEG analyzer function of the detection subsystem 322 are in communication; this facilitates the ability of stimulation subsystem 324 to provide responsive stimulation as well as an ability of the detection subsystem 322 to blank the amplifiers while stimulation is being performed to minimize stimulation artifacts. It is contemplated that the parameters of the stimulation signal (e.g., frequency, duration, waveform) provided by the stimulation subsystem 324 would be specified by other subsystems in the control module 310.

Also in the control module 310 is a memory subsystem 326 and a central processing unit (CPU) 328, which can take the form of a microcontroller. The memory subsystem 326 is coupled to the detection subsystem 322 (e.g., for receiving and storing data representative of sensed EEG signals and evoked responses), the stimulation subsystem 324 (e.g., for providing stimulation waveform parameters to the stimulation subsystem), and the CPU 328, which can control the operation of the memory subsystem 326. In addition to the memory subsystem 326, the CPU 328 is also connected to the detection subsystem 322 and the stimulation subsystem 324 for direct control of those subsystems.

The memory subsystem 326 may include one or more types of memory, including for example, random access memory (RAM), read only memory (ROM), and non-volatile memory (NVM). As explained further below, within one or more of the types of memory, such as RAM, there may be sections of memory reserved for the following: 1) EEG waveform data (stored ECoG's), 2) detailed event data regarding detection activity, 3) long-term histogram data on detections, and 4) device diagnostic information (battery voltage, lead impedance, radio usage, etc)

Also provided in the control module 310, and coupled to the memory subsystem 326 and the CPU 328, is a communication subsystem 330. The communication subsystem 330 enables communication between the implantable medical device 204 (FIG. 2) and the outside world, e.g., the data retrieval apparatus 206 (FIG. 2). The communication subsystem 330 may include a telemetry coil (which may be situated outside of the housing) enabling short-range transmission and reception of signals, to or from the implantable medical device 204, via inductive coupling. The communication subsystem 330 may also include a transceiver and one or more antennas for long-range telemetry by an RF communications link with the implantable medical device 204.

Rounding out the subsystems in the control module 310 are a power supply 332 and a clock supply 334. The power supply 332 supplies the voltages and currents necessary for each of the other subsystems. The clock supply 334 supplies substantially all of the other subsystems with any clock and timing signals necessary for their operation.

While the memory subsystem 326 is illustrated in FIG. 3 as a separate functional subsystem, the other subsystems may also require various amounts of memory to perform the functions described above and others. Furthermore, while the control module 310 is preferably a single physical unit contained within a single physical enclosure, namely the housing, it may comprise a plurality of spatially separate units each performing a subset of the capabilities described above. Also, the various functions and capabilities of the subsystems described above may be performed by electronic hardware, computer software (or firmware), or a combination thereof.

Figure 4:
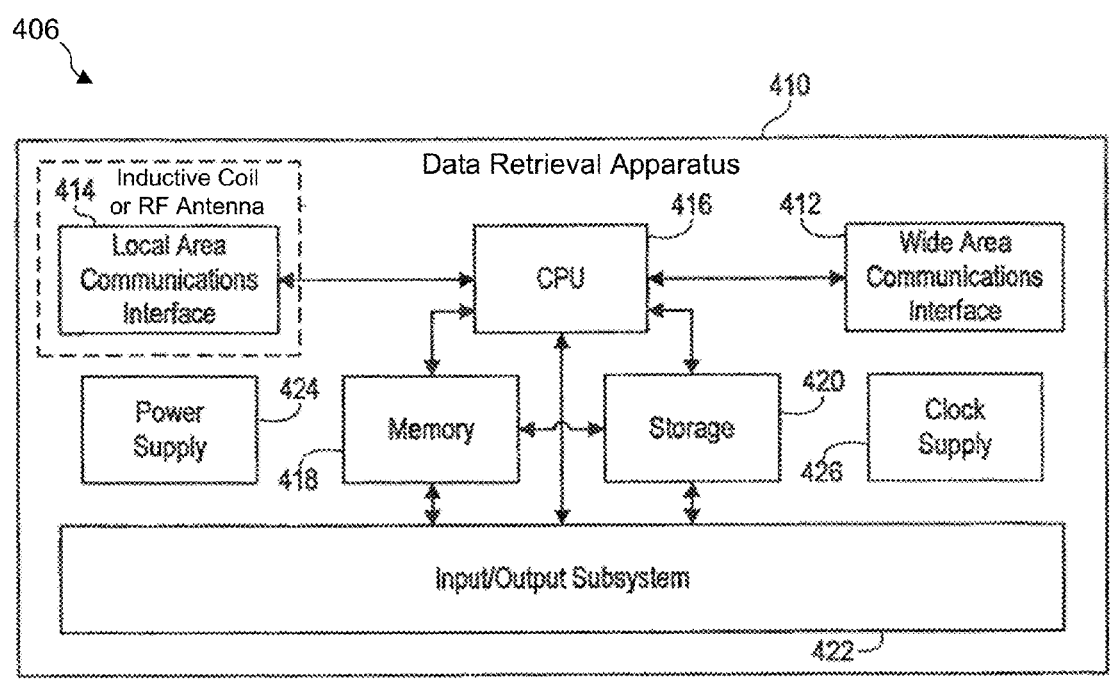
FIG. 4 is a block diagram of a data retrieval apparatus.

Referring now to FIG. 4, a block diagram representing a data retrieval apparatus 406 is set forth in detail. The data retrieval apparatus 406 includes a general-purpose or special-purpose computer programmed or adapted for use as described herein. The data retrieval apparatus 406 includes a wide area communications interface 412 for communications with the communications network 202 (FIG. 2), and a local area communications interface 414 for communications with the implantable medical device 204. The wide area communications interface 412 may be, for example, an Internet connection. The local area communications interface 414 may be an inductive short-range telemetry system including an inductive coil, or a long-range RF telemetry system including an RF antenna. The method and apparatuses disclosed herein are primarily directed to RF telemetry communications. Preferably, both the wide area communications interface 412 and the local area communications interface 414 are capable of bi-directional communications.

The data retrieval apparatus 406 is controlled by a CPU 416. The CPU is coupled, either directly or through a bus controller, to the wide area communications interface 412, the local area communications interface 414, a memory subsystem 418 for programming and short-term storage, a storage subsystem 420 (which might include a hard drive, flash memory, and other non-volatile storage), and an input/output subsystem 422 used to pass information to and receive information from a user. The memory subsystem 418 may include ROM, dynamic RAM, and other random-access memory. The storage subsystem 420 may include a hard drive, flash memory, and other non-volatile storage.

The operation of the data retrieval apparatus 406 is controlled by a power supply 424 and a clock supply 426. The power supply 424 typically includes batteries. Alternatively, the data retrieval apparatus 406 may receive power from an AC outlet. A combination of the two sources might also be used. The clock supply 426 supplies substantially all of the other subsystems of the network unit with any clock and timing signals necessary for their operation.

As with the implantable medical device 304 (FIG. 3) described above, while the memory subsystem 418 is illustrated in FIG. 4 as a separate functional subsystem, the other subsystems may also require various amounts of memory to perform the functions described herein and others. Furthermore, while the data retrieval apparatus 406 is preferably a single physical unit contained within a single physical enclosure, namely the housing, it may comprise a plurality of spatially separate units each performing a subset of the capabilities described herein.

The various functions and capabilities of the subsystems of the data retrieval apparatus 406 described above may be performed by electronic hardware, computer software, or firmware, or a combination thereof. The illustration of FIG. 4 shows several of the major functional subsystems present in a data retrieval apparatus consistent with the invention. However, in many computing systems, other functional subsystems and modules are present that are not necessarily reflected in FIG. 4. Moreover, a data retrieval apparatus 406 may integrate two or more of the above-referenced subsystems. For example, the wide area communications interface 412 and the local area communications interface 414 might be adapted into a single subsystem if efficiencies result there from. Accordingly, FIG. 4 is for purposes of illustration only, and does not necessarily reflect the actual configuration of the data retrieval apparatus. It is, however, considered to be representative.

Figure 5:
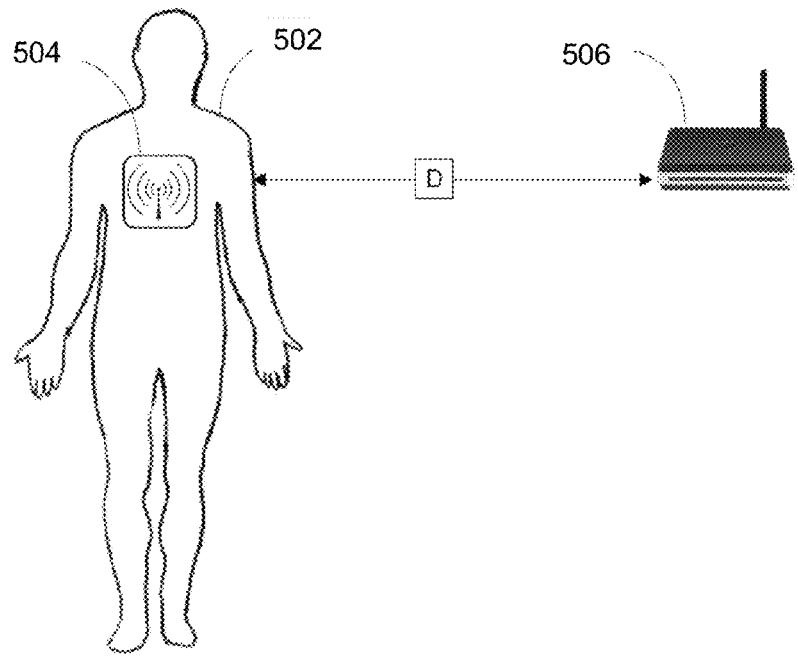
FIG. 5 is a diagram of a patient with an implantable medical device located near a data retrieval apparatus.

For a battery powered implantable medical device, minimizing power consumption during RF data transmission is very important because the implanted power source has a limited useful life (even in the case of an implantable medical device with a rechargeable battery). The geometrical considerations relative to an implantable medical device communicating via wireless telemetry are shown in FIG. 5. A patient 502 is shown with an implantable medical device 504 that has an approximately isotropic antenna capable of establishing a wireless telemetry link with a data retrieval apparatus 506. The data retrieval apparatus 506 that is located a separation distance D from the patient 502. An approximately isotropic antenna is desired to insure that the implantable medical device 504 could reliably establish a connection with the data retrieval apparatus 506 regardless of the orientation of the patient with respect to the data retrieval apparatus. Because an implantable medical device 504 is constrained in size and therefore has a relatively small antenna size (e.g., 1-10 cm) compared to the separation distance D (e.g., 1-5 m), the RF electric field strength produced at the data retrieval apparatus 506 by the implantable medical device 504 for a given transmission power will follow an approximately $1/R^2$ drop off and will correlate with the signal-to-noise ratio (SNR) measured at the data retrieval apparatus 506 for a given noise environment.

Direct measurement of signal-to-noise is not always practical, so often alternative methods may be used to assess signal strength. One alternative method of signal strength is referred to as the received signal strength indication (RSSI). The received signal strength indication metric describes the power present in a received radio signal typically in arbitrary units that can be reported as a DC voltage or as a digital value (e.g., 0 to 255 levels). The received signal strength indication correlates with the signal-to-noise for a given noise environment with higher received signal strength indication correlating with higher signal-to-noise.

Another alternative method of assessing signal strength is to measure the number of communication retries or correctable errors encountered during data transfer. Most digital communication protocols have a low level means of assessing whether a small portion of data (typically called a packet) of the total data digital transmission was communicated correctly. Two such methods are use of a parity bit or a cyclic redundancy check (CRC). These methods are well known to those skilled in the art and are not described in detail here. Essentially each method involves the inclusion of small amount of additional data (parity bit or check value) that mathematically describes the actual data being sent. As packet data are received, the test data are compared to the actual data per the defined relationship on a packet by packet basis to detect errors in the transmitted data. If an error is detected, retransmission of the packet is triggered. More advanced systems include error-correction codes which allow recovery of a packet of data with a small number of errors. However, if the number of errors exceeds the number of correctable errors, then the errors are considered "uncorrectable" and the entire packet of data is retransmitted. By assessing a series of data packet transmissions, the packet error rate (PER) can be determined by dividing the number of incorrectly transmitted packets by the total number of transmitted packets. The packet error rate will inversely correlate with the signal-to-noise with lower packet error rate correlating with higher signal-to-noise.

In the descriptions that follow the term signal-to-noise is generally used as the metric to describe the signal level, however, it should be understood that alternative methods of signal strength measurement such as received signal strength indication or packet error rate could be used as the signal strength metric for the methods described herein. Furthermore, because this disclosure does not address methods of signal strength assessment, but rather methods of optimizing data transfer using signal strength metrics, other methods of measuring signal strength not described herein could be used for the implementation of the techniques disclosed herein as well and use of such alternatives would not alter materially such techniques.

Referring to FIG. 5 again, at a distance of 1 m, the signal-to-noise may be X, but at 2 m the signal-to-noise will be reduced to X/4, and at 3 m the signal-to-noise will be reduced to X/9. Thus increasing the distance D reduces the signal-to-noise measured at the data retrieval apparatus, and eventually the signal-to-noise becomes too low and communication errors may result. The RF transmission power of the implantable medical device 504 may be increased to correspondingly increase the signal-to-noise, but such increased transmission power comes at the expense of more rapidly depleting the implantable medical device 504 battery.

Another option is to slow the data rate. Shannon's Channel Capacity Theorem, defines the maximum rate C of reliable (error-free) information transmission through a digital communications channel with bandwidth B as a function of the signal-to-noise as follows:

$$C = B \times \log_2(1+\text{signal-to-noise}) \text{ bits/sec} \qquad (\text{Eq. 1})$$

Figure 6:
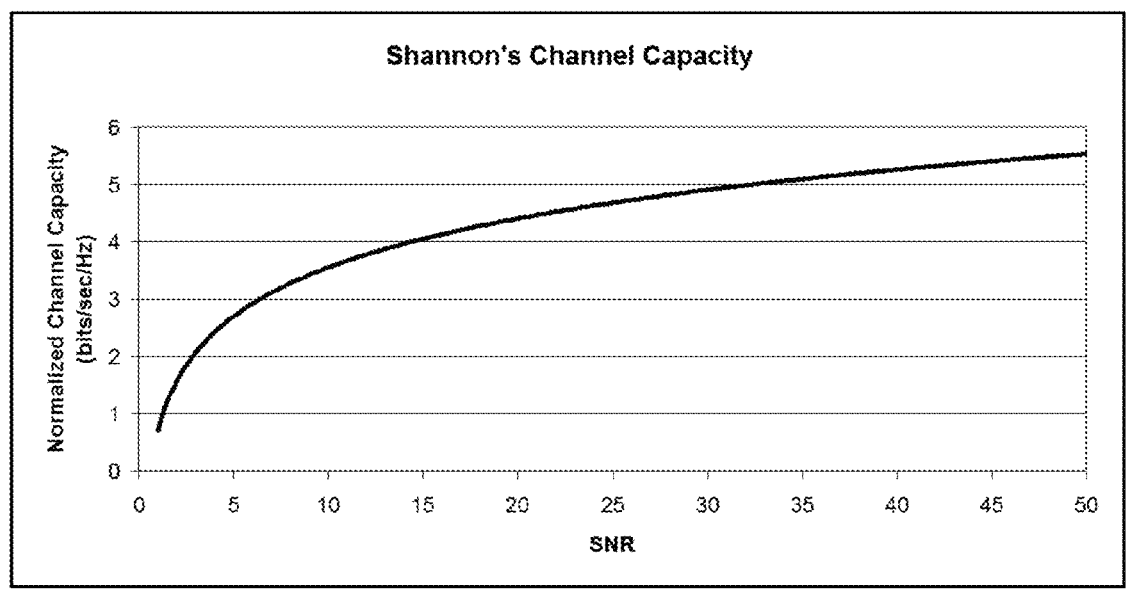
FIG. 6 is graph illustrating a communication quality measurement as a function of communication performance.

The relationship is plotted in FIG. 6 normalized per Hz of bandwidth. As the signal-to-noise is decreased, the data rate for reliable communications decreases with the greatest rate of change occurring at lower signal-to-noise values. As a result, at greater separation distances D, the data rate from the implantable medical device 504 to the data retrieval apparatus 506 could be reduced to allow communications at the lower signal-to-noise; however, it would then take longer to transmit the data, which also results in additional energy consumption.

Based on the above considerations, data retrieval ideally should be performed at a time when the distance D is minimized for a sufficient period of time for data retrieval to occur, which could take several minutes, to minimize the implantable medical device 504 battery energy used.

Figure 7:
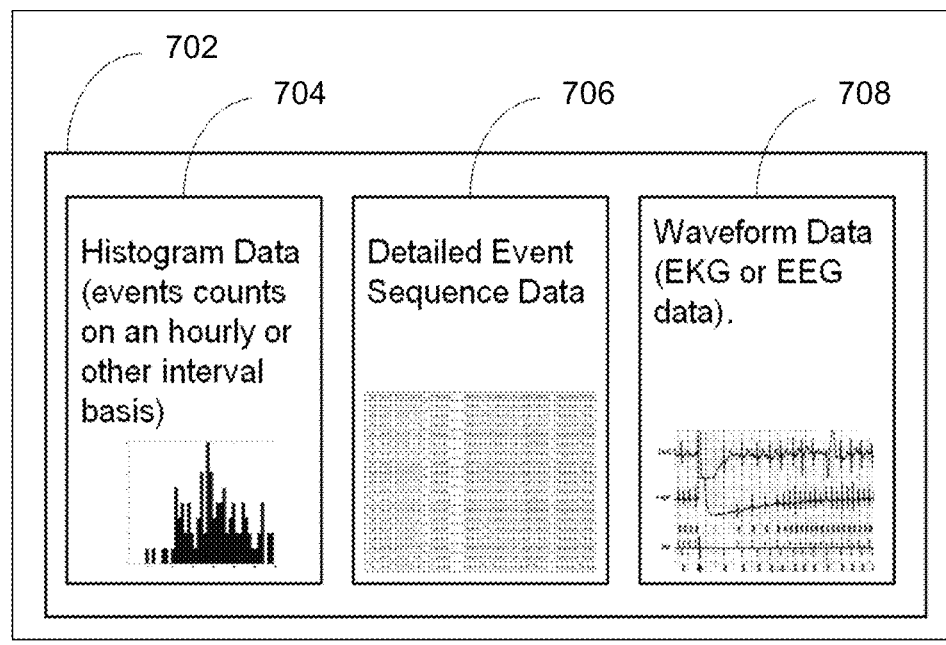
FIG. 7 is a diagram of data types and memory allocation in an implantable medical device.

Another consideration for data retrieval is determining when data retrieval is required to avoid data loss. It is likely that an implantable medical device 504 is configured to store different types of data. This concept is illustrated in FIG. 7 where the implantable medical device memory 702 is shown subdivided into sections, with a different type of data allocated to each section. The sections shown here are for illustrative purposes and a specific implantable medical device may have additional or different sections.

An implantable medical device can be configured to store different types of data in different sections of memory as shown in FIG. 7 when different events occur. For example, an implantable medical device 204 may be configured to detect a specific pattern present in a biological waveform. If this pattern occurs it may result in data storage in one section of memory, but not in another section of memory. Alternatively it could result in storage in multiple sections of memory in different forms as will be described. These sections of memory are associated with specific data types and are referred to in association with the type of data (e.g., histogram data memory), however, all types of data memory refer to sections of the memory subsystem 326 (FIG. 3), which may include one or more of RAM and non-volatile memory.

With reference to FIG. 7, histogram data memory 704 is used for counting the number of events for which it is configured to store information within a series of fixed time windows that extend over a multiple of such time windows. For example, an implantable medical device may count four different types of events on an hourly basis for the past 10 days. In this case, the implantable medical device has 4 bins for every hour for 10 days (4 bins×24 hours×10 days) and would likely not overwrite histogram data memory 704 prior to 10 days elapsing since the data was last transferred.

With continued reference to FIG. 7, detailed event sequence data memory 706 is used to store highly time accurate (e.g., to the second) information about physiological events. The data stored in this memory differs from the histogram data stored in the histogram data memory 704 in that it records the type and order of occurrence of events along with the exact time of occurrence. For example, if two "A type", one "B type" and one "C type" events occurred within a given hour, and the histogram data memory 704 was configured to store information for A and B events, and the event sequence data memory 706 was configured to store information on A, B and C type events, these different types of memories might record the following:

| Histogram data memory 704 | Detailed event sequence data memory 706 |
|---|---|
| A = 2, B = 1 (from 1:00-2:00) | A occurred at 1:23:21 |
|  | B occurred at 1:25:33 |
|  | C occurred at 1:38:44 |
|  | A occurred at 1:55:12 |

Hence, the detailed event sequence data memory 706 captures the order and timing of the events, whereas the histogram data memory only captures the total count of events within regularly spaced elapsed time intervals. As a result, a fixed amount of detailed event sequence data memory 706 fills at different rates depending on the rate of event occurrence. For example, the detailed event sequence data memory 706 may fill at a faster rate when events are happening at a faster rate. Accordingly, the elapsed time until overwrite of this data type varies.

The final type of memory in FIG. 7 is waveform data memory 708. This type of memory is generally used for storage based on the occurrence of specific events, referred to herein as "waveform data events." Waveform data events may or may not trigger storage in the other two types of aforementioned memory. Waveform data memory 708 is generally configured to store several separate waveform data events. The waveform data memory 708 used to record these waveform data events is generally configured to record a plurality of events in sequence. For example, the implantable medical device may be configured to store three such waveform data events, and in this case overwrite occurs after the fourth waveform data event occurred.

Figure 8A:
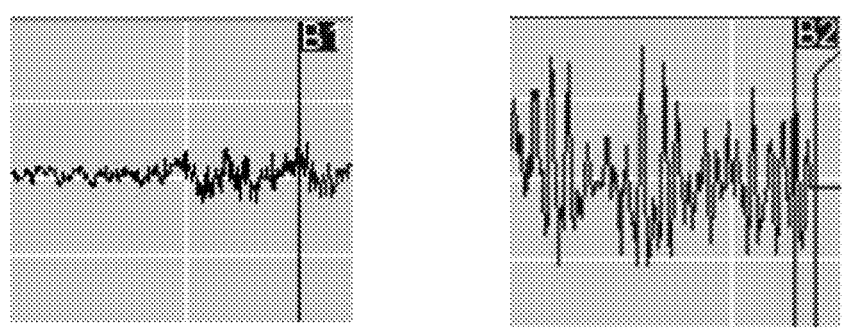
FIG. 8A are illustrations of physiological waveforms detected by an implantable medical device.

With reference to FIG. 8A, an example further illustrating these data types and their interrelationships is shown for an implantable medical device that is a responsive neurostimulation system for epilepsy. For this system the implantable medical device would be connected to electrodes that are implanted in the brain that are used for delivering electrical stimulation to the brain to reduce seizures. In this case the implantable medical device has been programmed to detect two patterns present at seizure onset and to provide stimulation therapy for either. Referring to FIG. 8A, pattern B1 is a 40 Hz low-amplitude signal, and pattern B2 is an approximately 20 Hz higher amplitude signal.

The histogram data 704 (FIG. 7) for these events for a seven day period are shown in FIG. 8B, where the y-axis amplitude represents the number of events for each pattern that occurred within one hour bins. Note that these data do not indicate when the events occurred within the hour, nor do they indicate the relationships between subsequent events. These data do show that pattern B1 occurs more frequently and has daily periods where it is more frequent, whereas pattern B2 occurs relatively infrequently.

Figure 8C:
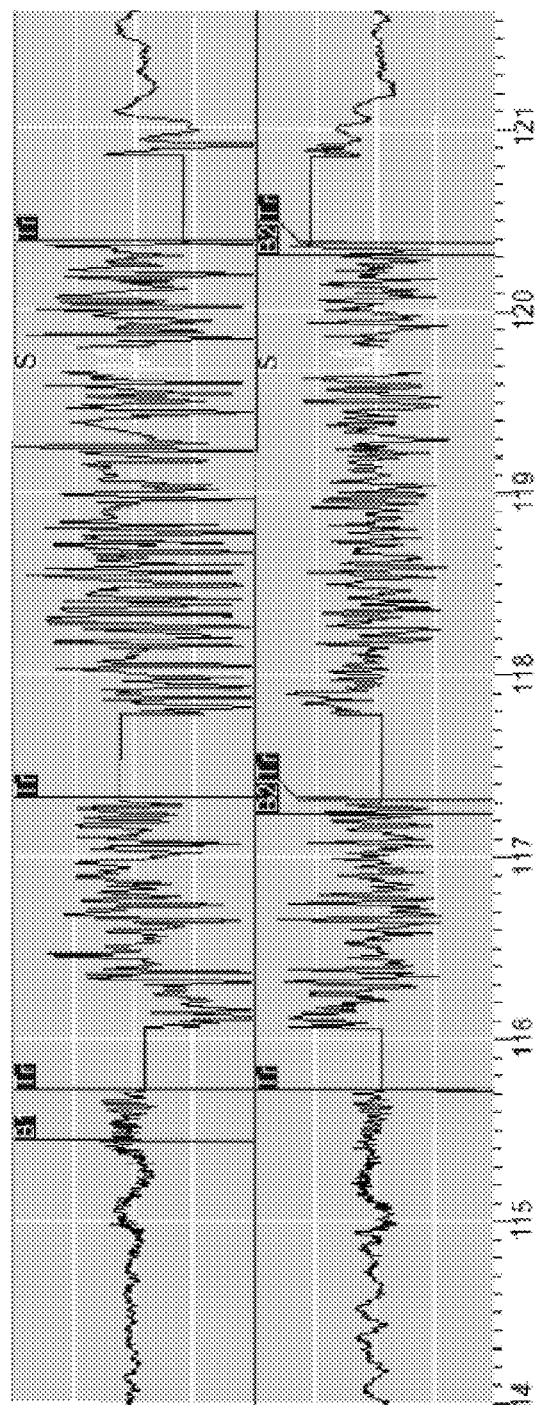
FIG. 8C are illustrations of detailed physiological waveforms recorded by an implantable medical device.

Detailed event sequence data 706 (FIG. 7) and waveform data 708 are shown for a common data sequence in FIG. 8C. The top panel shows the detailed event sequence data 706 in time order of occurrence. These data are very useful for devices that deliver stimulation therapy in sequence where each therapy may differ to assess the effectiveness of different therapies. These data may also provide insight into event durations. The bottom panel of FIG. 8C shows the waveform data 708, which in this case is electrocorticogram (ECOG) data. The waveform data 708 are particularly useful for assessing the effectiveness of the detection relative to the observed pattern. In addition, waveform data 708 are useful for monitoring electrode operation and can help diagnose electrode malfunctions which produce noise distinctly different from normal signals that a trained observer can easily detect.

Figure 9:
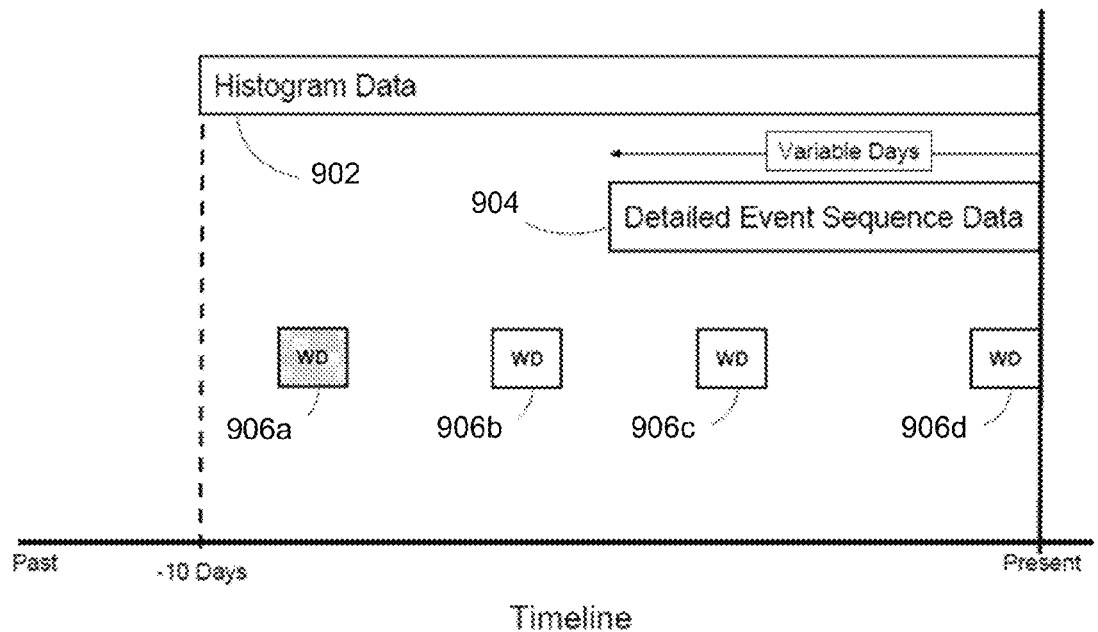
FIG. 9 is a timeline illustrating three different data types recorded by an implantable medical device.

The timelines covered by the types of memory 704, 706, 708 are shown in FIG. 9 for the situation where data transfer occurs at the present time, which is at the right side of the graph. Histogram data 902 covers a fixed period of time, for example the past 10 days. Detailed event sequence data 904 is continuous in nature, but the amount of time covered prior to overwrite is variable and depends on patient activity. Waveform data events 906a-906d occur sporadically and are not continuous like the two aforementioned data types. In FIG. 9 the implantable medical device is configured to store three waveform data events 906 and data transfer once again occurs at the present time. The waveform data events would be stored sequentially with 906a being stored first followed by 906b and 906c. However, when event 906d occurs, the implantable medical device must either overwrite the oldest waveform data 906a or not record the latest waveform data event 906d. In this example the shading of waveform data event 906a indicates that the data event 906a has been overwritten.

Peak Signal Strength Time Adaptation

To minimize RF power consumed by the implantable medical device during data retrieval, a patient should be as close to a data retrieval apparatus as possible for the period of time needed for data retrieval, which could be several minutes depending on the amount of data, the system design, the ambient background electromagnetic noise or other factors. One approach is to locate the data retrieval apparatus near the patient's bed, possibly on a bedside stand, and then to perform the data retrieval when the patient is asleep and thus likely to remain in the same general area relative to the data retrieval apparatus. One way of realizing this goal is for the physician to ask the patient about their sleep cycle and then to have a programmable data retrieval time setting in the data retrieval apparatus that results in data retrieval occurring at a fixed time based on the information the patient provides about when he or she usually is in bed and/or asleep. The disadvantages of this approach are that it requires additional effort by the physician, is subject to programming errors by the physician and sleep reporting errors by the patient, and it is not robust relative to changes in the patient's sleep cycle that may occur due to travel, time-zone changes, or lifestyle changes such as work or school schedule changes.

In accordance with techniques disclosed herein, an alternative approach involves ascertaining the patient's proximity to the data retrieval apparatus by briefly establishing RF telemetry during a calibration period (and recalibration periods, if necessary) so that the data retrieval apparatus can automatically adapt to the patient's likely sleep cycle.

Figure 10:
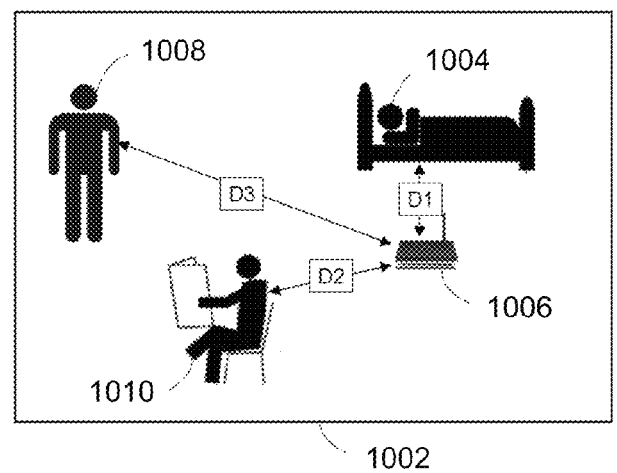
FIG. 10 is a schematic diagram illustrating various location of a patient relative to a data retrieval apparatus.

With reference to FIG. 10, three possible conditions that might occur during the course of the day are shown. Within the patient's bedroom 1002, the data retrieval apparatus 1006 is located near the patient's bed. In one situation 1004 the patient is in bed and the data retrieval apparatus 1006 is located a distance D1 away. In a second situation 1010 the patient is sitting and the data retrieval apparatus 1006 is located a distance D2 away, which is twice as distant as D1. In a third situation 1008 the patient is in the room further away and the data retrieval apparatus 1006 is located a distance D3 away, which is three times as distant as D1.

Figure 11:
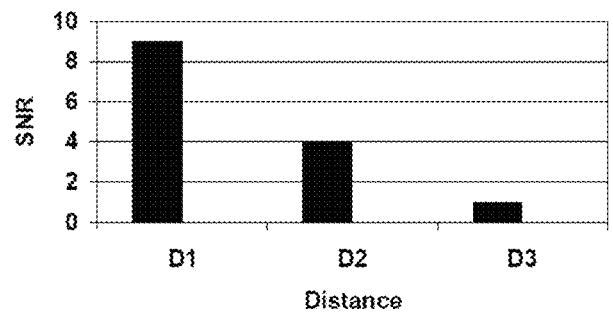
FIG. 11 is a graph illustrating a communication quality measurement for each of the patient location positions of FIG. 10.

If the data retrieval apparatus 1006 establishes a telemetry link with the implantable medical device, the RF electric field strength produced by the implantable medical device at the data retrieval apparatus 1006 would be a function of the separation distance D1, D2, D3 and would correlate with the signal-to-noise measured by the data retrieval apparatus for a given noise environment. Exemplary signal-to-noise measurements corresponding to the three distances D1, D2, D3 are shown in FIG. 11.

As previously described, retrieving data from the implantable medical device when the patient is in the closest proximity (such as when they are in bed when the data retrieval apparatus is located very near to the bed), maximizes the signal-to-noise. This allows the highest data rate for a given design and power level, and minimizes the battery energy used by the implantable medical device to transmit the data.

To determine when the patient is positioned so as to allow for a maximum signal-to-noise, or an signal-to-noise above a threshold criterion, a calibration method may be used.

During calibration the data retrieval apparatus 1006 opens a communications channel with the implantable medical device to measure the signal-to-noise on the communications channel. The data retrieval apparatus 1006 does this in a periodic and systematic manner. For example, calibration may occur by having the data retrieval apparatus 1006 periodically (e.g., every 30-60 minutes) open the communications channel very briefly with the implantable medical device to assess the communications channel signal-to-noise. The duration of the communications may be the minimum needed to measure the signal-to-noise at that instant and hence may be short and accordingly, consume minimal battery energy.

Various methods for assessing the signal-to-noise of the communications channel can be implemented by one skilled such as examining a carrier or demodulated signal voltage in an amplifier stage, or by monitoring the gain needed to amplify the signal to the appropriate level for the detection circuit used for decoding. As previously described, the received signal strength indication could also be used as the metric for this method.

Figure 12:
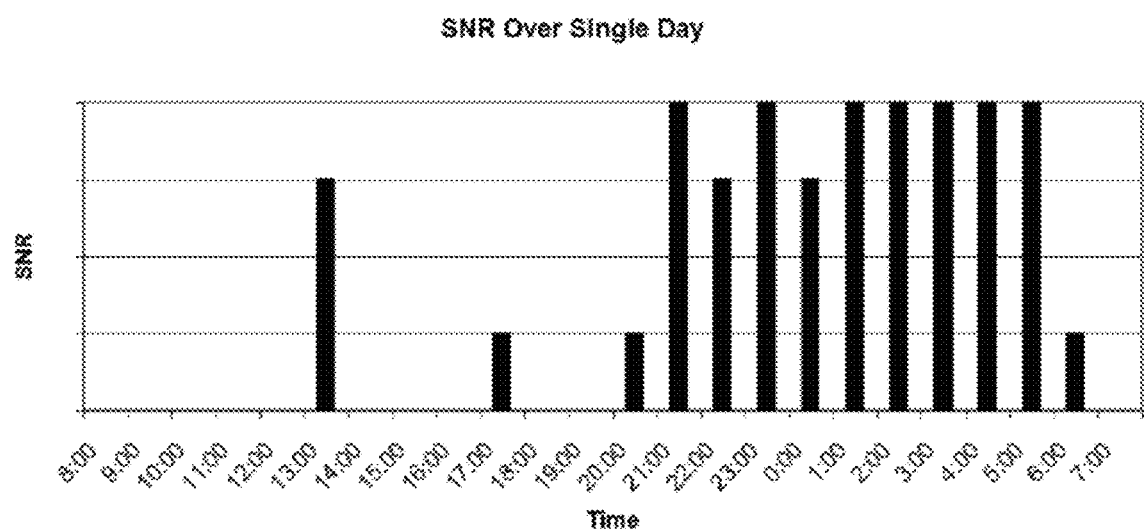
FIG. 12 is a graph illustrating various communication quality measurements as a function of time of day.

The result of this process for a representative single day is illustrated in FIG. 12, which shows individual signal-to-noise measurements as sampled every 60 minutes over a 24 hour period beginning at 8:00. In this example the signal-to-noise measurements are at their highest values continuously for the samples between 21:00 and 05:00. This pattern of signal-to-noise measurements indicates a pattern of close proximity between the implantable medical device and the data retrieval apparatus, suggestive of patient sleep between those times.

Because sleep patterns vary, and sample times may occur when a patient is momentarily absent from the bed over the course of the night for micturition or other reasons, a more robust approach would be to sample over multiple days (e.g., 3-10 days). An exemplary result of this process for a representative calibration period is shown in FIG. 13 in tabular form, which includes the signal-to-noise measurements as sampled every 60 minutes per day, over a seven day period. In this example, the signal-to-noise has levels between 0 and 4. Different embodiments may have different signal-to-noise range resolutions, but the same calibration principles would apply. The bottom line of the table in FIG. 13 shows the average signal-to-noise measured for each hour (e.g., 02:00) over the 7 day calibration period.

Figure 14:
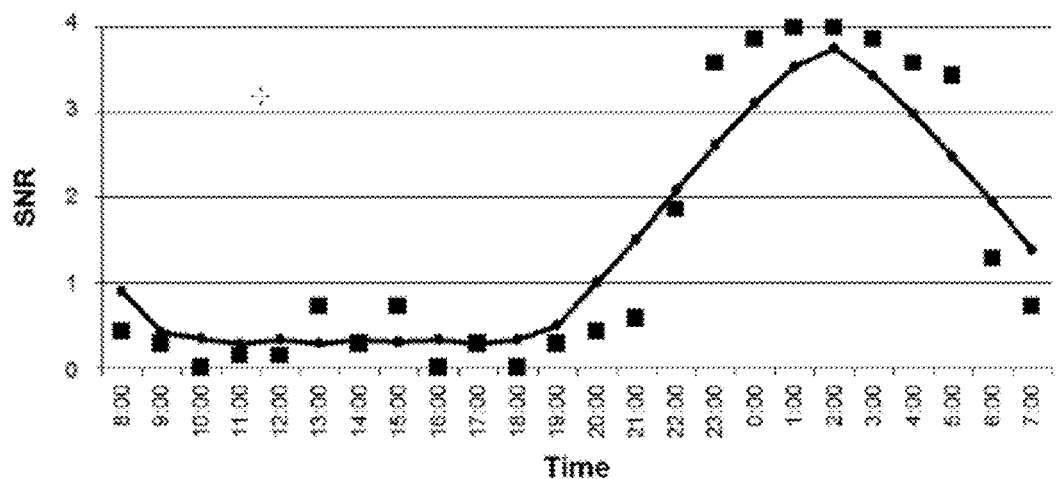
FIG. 14 is a graph illustrating a curve fitted to communication quality measurements spanning a 24 hour period.

The average signal-to-noise values shown in the table of FIG. 13 are plotted in FIG. 14. The values shown by the non-connected squares are the average signal-to-noise values over seven days for that time period. For example, at 10:00 the signal-to-noise is zero, meaning the data retrieval apparatus 1006 (FIG. 10) was unable to establish a communications channel with the implantable medical device on any of the seven days during the calibration period. It will be beneficial to transfer data at a time when the patient is in very close proximity to the data retrieval apparatus for the complete time needed to transfer all data at the fastest possible data rate, such as when the patient is in bed sleeping. Sleep periods could be inferred for times when the signal-to-noise is maximized for long periods, such as six to eight hours. To determine probable times when sleep occurs, it would be beneficial to filter the signal-to-noise time plot. Many filtering methods are implementable by one skilled in the art. In FIG. 14 a rectangular (sinc) filter has been applied to create the smoothed line plot. This filter uses 7 hours of data, which would tend to create a single peak for a patient that slept a typical 7 hours per night. The operation of the filter applied in this example is described mathematically below where $\overline{SNR_i}$ represents the average signal-to-noise for hour i (e.g., 02:00) over the entire 7 day calibration period.

$$\overline{SNR_i} = (SNR_{i-3} + SNR_{i-2} + SNR_{i-1} + SNR_i + SNR_{i+1} + SNR_{i+2} + SNR_{i+3})/7 \quad (\text{Eq. 2})$$

Figure 15:
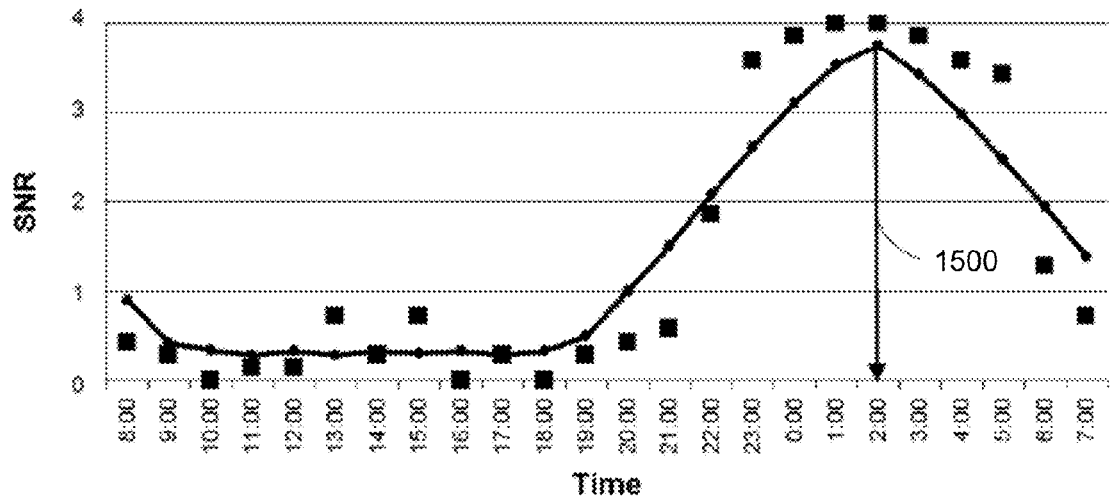
FIG. 15 is the graph of FIG. 14 further identifying a time of a peak communication quality measurement.

Various methods of optimizing the time for data retrieval are implementable by one skilled in the art. One method is to set the retrieval time for peak of the smoothed, average signal-to-noise data as shown by the arrow 1500 in FIG. 15. Another method is to specify what signal-to-noise is acceptable and to determine what time represents the midpoint of contiguous values where the smoothed, average signal-to-noise values exceed that level. This is shown in FIG. 1600 where the threshold level for an acceptable signal-to-noise is level 3, and the midpoint of the time when this is exceeded is shown by the arrow 1600.

These methods for determining optimum data transfer times could be triggered to re-run after an unsuccessful retrieval attempt, or after a series of unsuccessful interrogation attempts, to adjust to patients changing sleep patterns. In addition, this method may incorporate a start-up phase where a single day or a multiple of days less than the requisite calibration period number of days (7 days in the prior example) is used to schedule data retrieval time, in an albeit less optimized manner, prior to the elapse of the requisite calibration period number of days.

Figure 17:
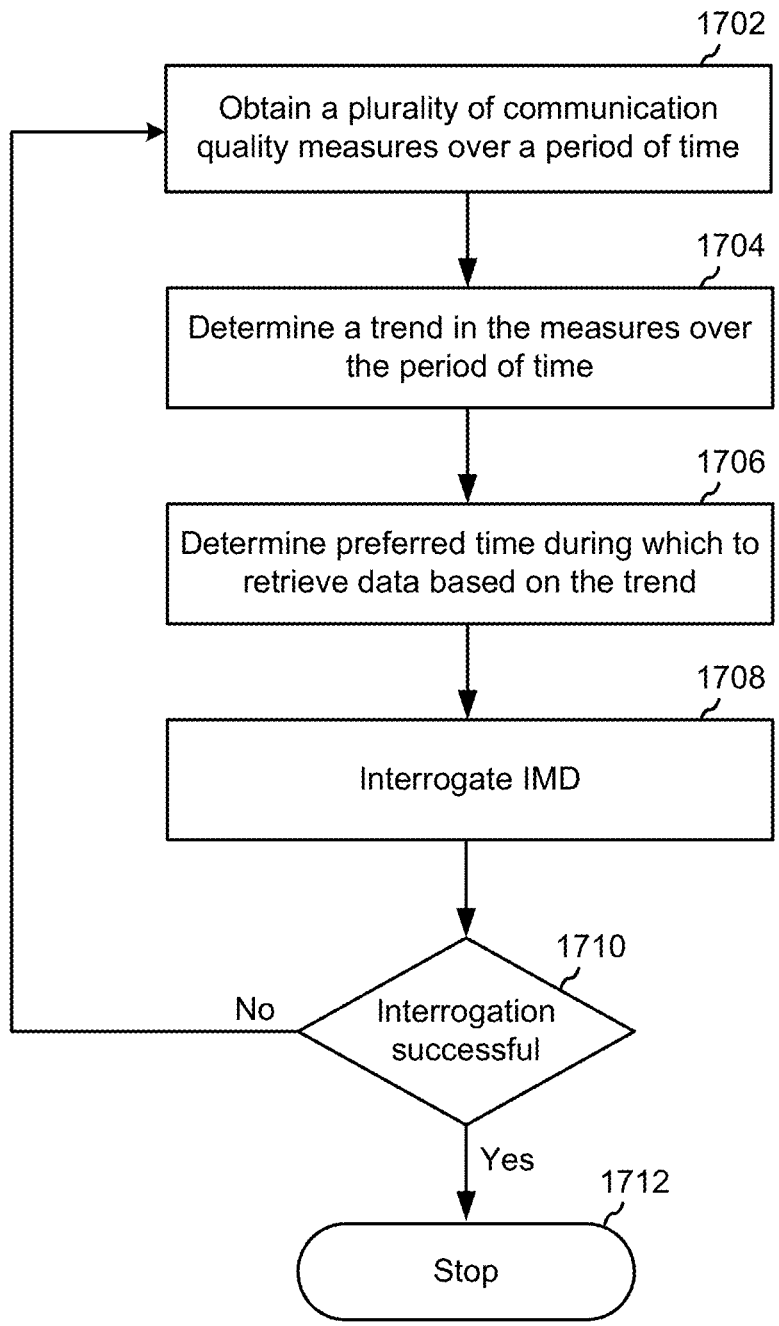
FIG. 17 is a flow chart of a method of retrieving patient data from an implantable medical device.

With reference to FIG. 17, a process for calibrating the retrieval of patient data from an active implantable medical device is shown. In summary, this process determines optimum times for data retrieval using the aforementioned calibration method that involves brief systematic and periodic signal strength determination combined with averaging and smoothing. Such a method maximizes the probability of data retrieval at the highest possible bandwidth for a given communications channel design and power level, which minimizes the energy an implantable medical device uses to transmit data and hence maximize battery longevity.

The process of FIG. 17 may be performed by a data retrieval apparatus configured to communicate with an active implantable medical device. The data retrieval apparatus obtains a number of measures over a first period of time (step 1702). The measures correspond to a quality of a communications channel between the data retrieval apparatus and the active implantable medical device. Such quality measures may include, for example, one or more of a signal-to-noise, a received signal strength indication, and packet error rate, or a combination thereof. As described above, the first period of time may range from 24 hours to any number of days, where the number of days may range from three days to ten days.

The data retrieval apparatus then determines a trend in the plurality of measures over the first period of time (step 1704). The trend may be determined by quantifying the obtained quality measures as a function of time. For example, the data retrieval apparatus may collect signal-to-noise measurements, and quantify those measurements as a function of time over a one day period, such as described above with reference to FIG. 12. The data retrieval apparatus may also quantify signal-to-noise measurements by determining, for each day within the first time period, signal-to-noise measurements for sub-time periods, e.g., hours, within the day. The data retrieval apparatus may then determine an average signal-to-noise for each sub-time period, over the entire time period. An example of quantifying measurements is this manner is shown and described above with reference to FIG. 13. A exemplary trend is represented by the data and fitted curve shown in FIG. 14.

Figure 16:
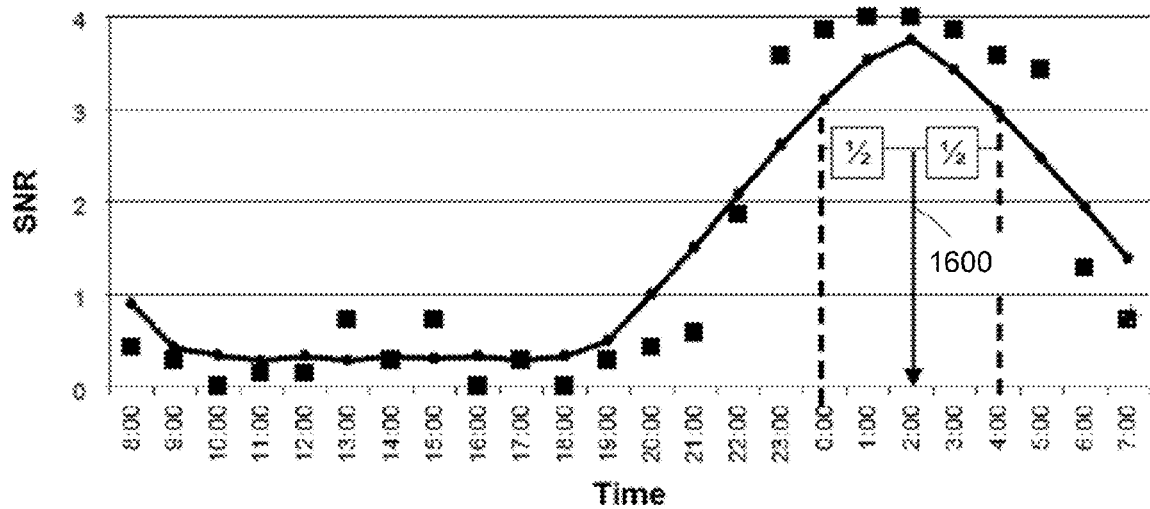
FIG. 16 is the graph of FIG. 14 further identifying a time range during which communication quality measurements satisfy a threshold.

The data retrieval apparatus determines at least one preferred time during which to retrieve data based on the trend (step 1706). To this end, the data retrieval apparatus further processes the quantified quality measurements, such as the average signal-to-noise, to identify a time or time duration during which one or more of the measurements indicate a higher quality of communication relative to other times or time durations. For example, the data retrieval apparatus may identify a time of day, e.g. hour, at which the quality of communication is at a peak (see, e.g., FIG. 15). Alternatively, the data retrieval apparatus may identify a time range, e.g., midnight to 4:00 am, during which the quality of communications satisfies a quality criterion. For example, the time range may correspond to a period of time during which the signal-to-noise is above a threshold value (see e.g., FIG. 16).

Subsequent to the calibration, the data retrieval apparatus interrogates the active implantable medical device to retrieve data during the preferred time (step 1708). Interrogation involves establishing a communications link with the active implantable medical device, sending a request for data to the medical device and receiving data from the medical device. The data retrieval apparatus monitors for unsuccessful interrogation attempts (step 1710). Such monitoring may involve the data retrieval apparatus not receiving an acknowledgement from the implantable medical device establishing a communication link. Alternatively, such monitoring may involve the data retrieval apparatus determining that a packet error rate in the communications link is below a threshold requirement indicative of quality data reception. The consequence of tolerating a large number of failed attempts is increased implantable medical device battery usage. Accordingly, if a prerequisite number of interrogation attempts are unsuccessful, the data retrieval apparatus executes a recalibration process by repeating the obtaining of a plurality of measures (step 1702), determining a trend (step 1704) and determining a preferred time (step 1706). The prerequisite number of failed attempts may be as little as one attempt, but may be programmable to a higher number based on performance of the RF communication link between the active implantable medical device and data retrieval apparatus. In one configuration, the recalibration process is streamlined relative to the initial calibration process in order to conserve power. To this end, during recalibration the data retrieval apparatus obtains quality measures over a time period that is less the prior period during which measures were obtained for the initial calibration. If interrogation (step 1710) is successful the data retrieval apparatus stops the process (step 1712).

Transmission Power Optimization using Signal Strength Feedback

Figure 18:
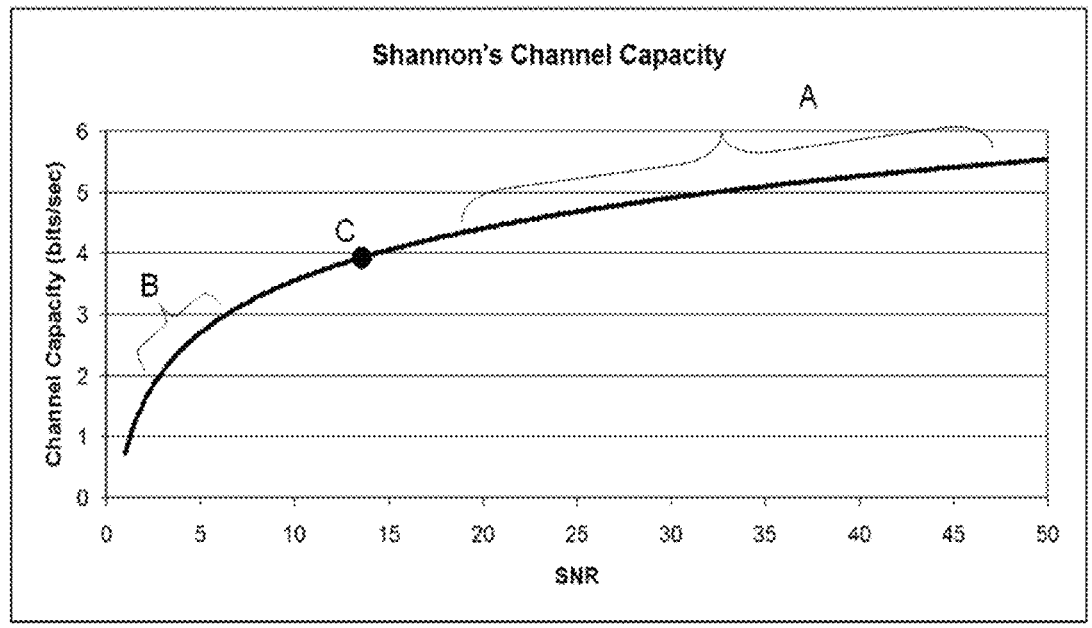
FIG. 18 is the graph of FIG. 6 further identifying periods corresponding to different rates of change in a communication quality measurement as a function of communication performance.

Based on the aforementioned methods for optimizing signal-to-noise, it also may be possible to lower the implantable medical device RF power level without significantly impacting data transfer rates to result in a net energy savings. Shown again in FIG. 18 is the relationship for Shannon's Channel Capacity Theorem, where the relationship between signal-to-noise quality measurements and communications link quality, e.g., channel capacity, are presented. A range of quality measurements, e.g., signal-to-noises, is identified as region "A." A communications link between an active implantable medical device and data retrieval apparatus having an signal-to-noise within the range of region "A" provides the channel capacity necessary for effective transfer of data between the devices. Using the methods previously described, a data retrieval apparatus may be configured to initiate data transfer when the implantable medical device is generally reliably in close proximity such that the signal-to-noise achieved is in region "A."

With continued reference to FIG. 18, the slope of the curve within region "A" is substantially small. Accordingly, for device communication operating within region "A," a change in RF power level has minimal impact on communications quality. In other words, as the RF power level of the implantable medical device is reduced and the signal-to-noise accordingly decreased, the impact on the channel capacity of a communications link is less pronounced than in other regions of the curve. For example, changes in RF power level in region "B" may have a severe impact on channel capacity.

Once the system has been optimized to operate in region "A" based on close proximity between the implantable medical device and the data retrieval apparatus, the data retrieval apparatus may feedback the signal-to-noise (or received signal strength indication or packet error rate) detected to the implantable medical device so that the implantable medical device RF transmission power level may be adjusted downward until the signal-to-noise reached a minimum threshold point "C." The minimum threshold represents a point below which channel capacity is inadequate to meet minimum data rate requirements.

Figure 19:
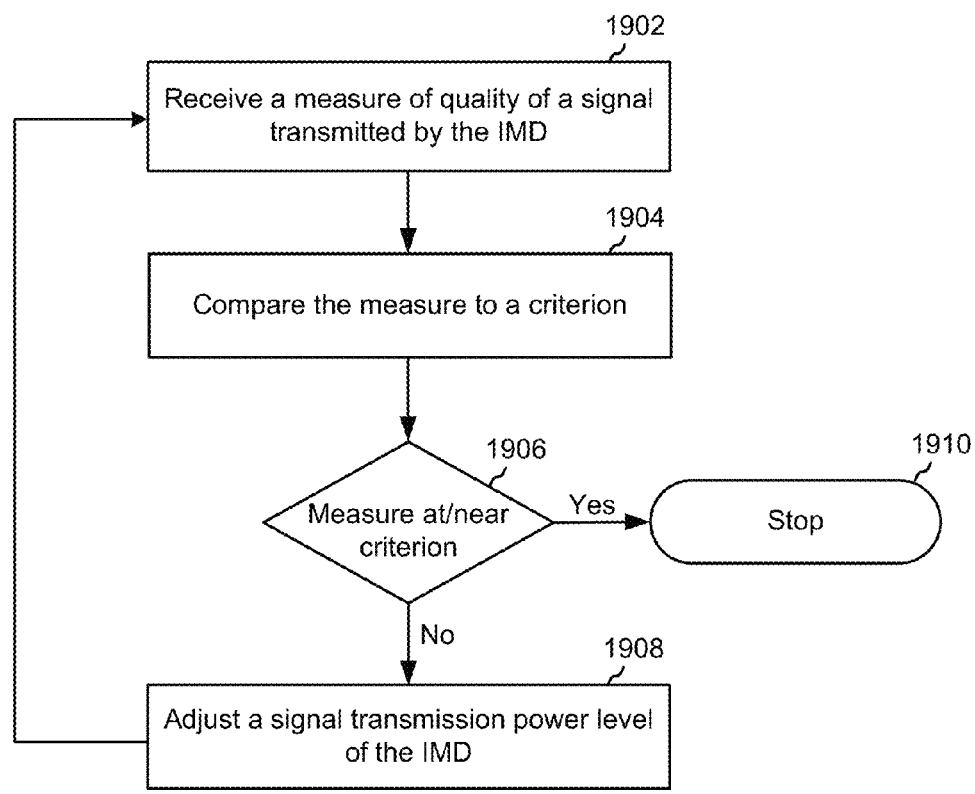
FIG. 19 is a flow chart of a method of adjusting power transmission of an implantable medical device.

With reference to FIG. 19, a process for adjusting the power transmission of an active implantable medical device is shown. In summary, the process provides for adjusting the active implantable medical device transmission power to the lowest level that supports a minimum performance requirement, such as a threshold channel capacity. A measure of signal strength of a signal transmitted by the active implantable medical device is feedback to the implantable medical device so that the RF transmission power can be reduced to the lowest level that supports the required data rate. The process minimizes the energy an implantable medical device uses to transmit data and hence increases battery longevity.

The process of FIG. 19 may be performed by an active implantable medical device configured to communicate with a data retrieval apparatus. The implantable medical device receives a measure of quality of a signal transmitted by the implantable medical device (step 1902). The signal transmitted by the implantable medical device may be sent to a data retrieval apparatus, in which case, the measure received by the implantable medical device is a feedback signal received from the data retrieval apparatus. The measure of quality may be one of a signal-to-noise, a received signal strength indication, or a packet error rate of the signal transmitted by the implantable medical device.

The active implantable medical device compares the measure to a criterion (step 1904). The criterion may be a minimum quality measure, below which a minimum performance requirement for communication may not be obtained. For example, with reference to FIG. 18 described above, in one configuration the minimum quality measurement is a signal-to-noise below which channel capacity is inadequate to meet minimum data rate requirements. In FIG. 18, the minimum quality measurement is the signal-to-noise corresponding to point "C", and the minimum performance requirement is the channel capacity corresponding to point "C".

Next, the active implantable medical device determines if the measure is at or near the criterion (step 1906). The intent is to have the implantable medical device reduce its transmission power to a level that causes the quality measure to closely approach the criterion without falling below it. To this end, if the measure is not at or near the criterion (step 1906), the implantable medical device adjusts, e.g., reduces, the signal transmission power level (step 1908), and the process is repeated until the measure satisfies the minimum criterion. If the measure is at or near the criterion (step 1906) the implantable medical device stops the process (step 1919). Alternatively, adjusting the signal transmission power may include increasing the power level, if the communications quality measure falls below the threshold.

Interrogation Frequency Adaptation

It is important that data be retrieved prior to data overwrite so that the physician obtains a complete understanding of implantable medical device performance. One way of realizing this goal is for the physician to program a data retrieval interval (e.g., every day, every three days, every week) that is frequent enough to avoid overwrite. The disadvantages of this approach are that it requires additional effort by the physician, is subject to programming errors by the physician, and different types of data require interrogation at different intervals as previously described. Furthermore, the rate of events that the implantable medical device stores in memory may vary with the patient's medical condition, which results in variations in the time before overwrite, and a fixed interval does not adjust to these variations.

An alternative to the fixed interval approach is to have the data retrieval apparatus asses memory availability as data is retrieved and then to schedule the next retrieval based on an estimate of when overwrite will occur.

Figure 20:
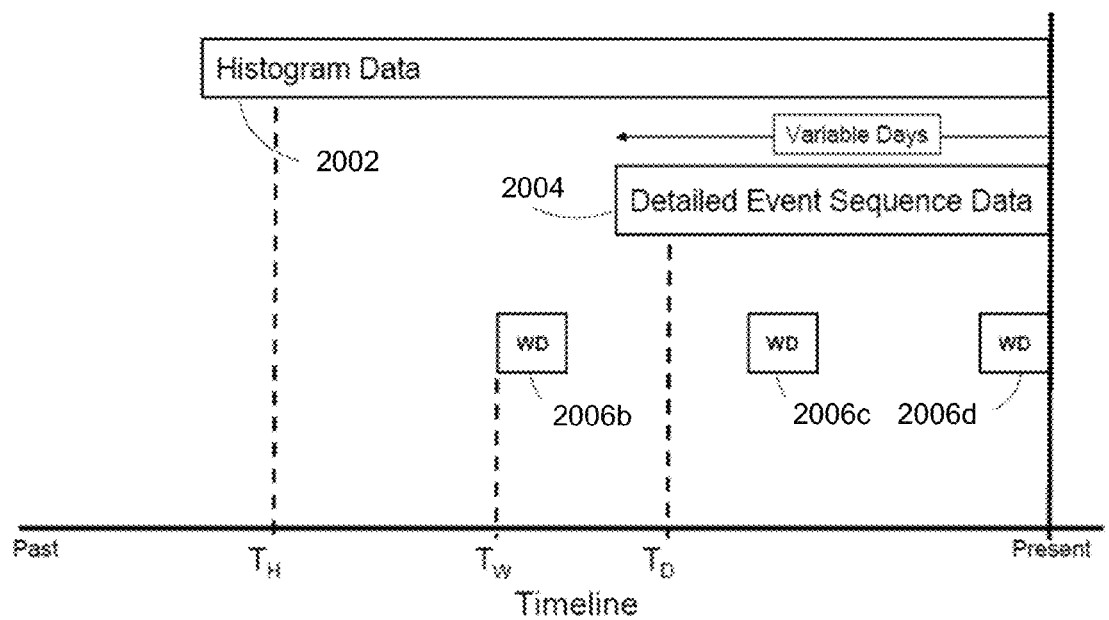
FIG. 20 is the timeline of FIG. 9 further identifying times at which different data types recorded by an implantable medical device are retrieved by a data retrieval apparatus.

With reference to FIG. 20, histogram data 2002 is fixed and may be scheduled for retrieval after an elapsed time of $T_H$ that is a percentage of the total histogram data time coverage period. The coverage time period is a programmed value and thus may be known by the data retrieval apparatus. For example, if the histogram data covers a ten day period, the data retrieval apparatus may schedule data retrieval every nine days to provide a safety margin in the event interrogation is unsuccessful on a given day.

Detailed event sequence data 2004 has variable time coverage as previously discussed with reference to FIG. 9. This data type includes event type and time of occurrence and is presented in order of occurrence. Upon data retrieval, the data retrieval apparatus may assess the past use of the memory portion allocated to this data type based on the retrieved data and schedule the next detailed event sequence data 2004 accordingly. For example, with reference to FIG. 20, the data retrieval apparatus may schedule the next retrieval at time $T_D$ that is a percentage of the elapsed time that the detailed event sequence data covers. In other words, the elapsed time may correspond to the time difference between the oldest event and the most recent event. In the event the data retrieval occurs prior to the detailed event sequence data 2004 memory being full, the percentage of memory used relative to the time coverage of that data may be used to estimate the time when the memory would have been full.

Waveform data 2006b, 2006c, 2006d is episodic. An approach for scheduling when waveform data retrieval should next occur is to schedule the next data retrieval to occur at a time interval equal to the time that has elapsed since the oldest waveform data event 2006c was stored. Referring to FIG. 20, if the implantable medical device can store three events, then waveform data 2006b is the oldest waveform and the next retrieval of waveform data may be scheduled based on the time of the occurrence of the oldest waveform. For example, referring again to FIG. 20, the time until the next retrieval would correspond to the elapsed time between the present time and the time of occurrence of waveform data 2006b, which is time $T_W$. Alternatively a safety margin could be applied and an interval that is a percentage of $T_W$ could be used (e.g., 90%×$T_W$). In the event that the memory allocated for waveform data is not full, the next waveform data retrieval could be scheduled to occur at longer time interval. For example, if the implantable medical device were configured to store three waveform events and the last waveform data retrieval interval was set for 24 hours, but only one waveform event were recorded, the retrieval interval could be increased to a longer interval than the prior interval by a fixed amount (e.g., 24 hours) or it could be increased based on the ratio of total available memory to the used memory (24 hours×3 events÷1 event used). In addition to the above fixed time values, statistical methods could be applied so that data retrieval intervals are scheduled at averages or medians of the times ($T_H$, $T_W$, $T_D$) measured on a plurality of occasions.

The data retrieval apparatus may incorporate programmable constraints that limit total data retrieval to avoid implantable medical device battery depletion. For example, data retrieval could be adaptable as described herein, but could be limited to occur no more frequently than every N days or some other interval that is acceptable relative to impact on battery longevity. Alternatively, the amount of data per unit time could be used as a constraint.

For example, 500 kilobytes per week (seven days) may be specified as a constraint for data retrieval. Using the methods described herein the data retrieval apparatus may determine that $T_W$, the time between waveform data retrieval, should be every day, however, after five days the amount of waveform data retrieved reaches 500 kilobytes, so the constraints then apply and additional waveform data are not retrieved. In other words, the scheduled data retrievals are subordinate to the data limit imposed by the data retrieval apparatus. After the period of time associated with the data limit has expired, another allocation of data amount, e.g., 500 kilobytes, becomes available and data retrieval may begin again according the schedule established by the data retrieval apparatus.

In this manner a precise limit on data transmitted can be applied, which should provide a predictable estimate of data transmission impact on implantable medical device battery longevity. Using either of the aforementioned methods (minimum time between interrogations or specified maximum amounts of data per time) do not preclude that the different data types described may have differing data limit constraints or that some data types may be unconstrained while others are constrained.

Figure 21:
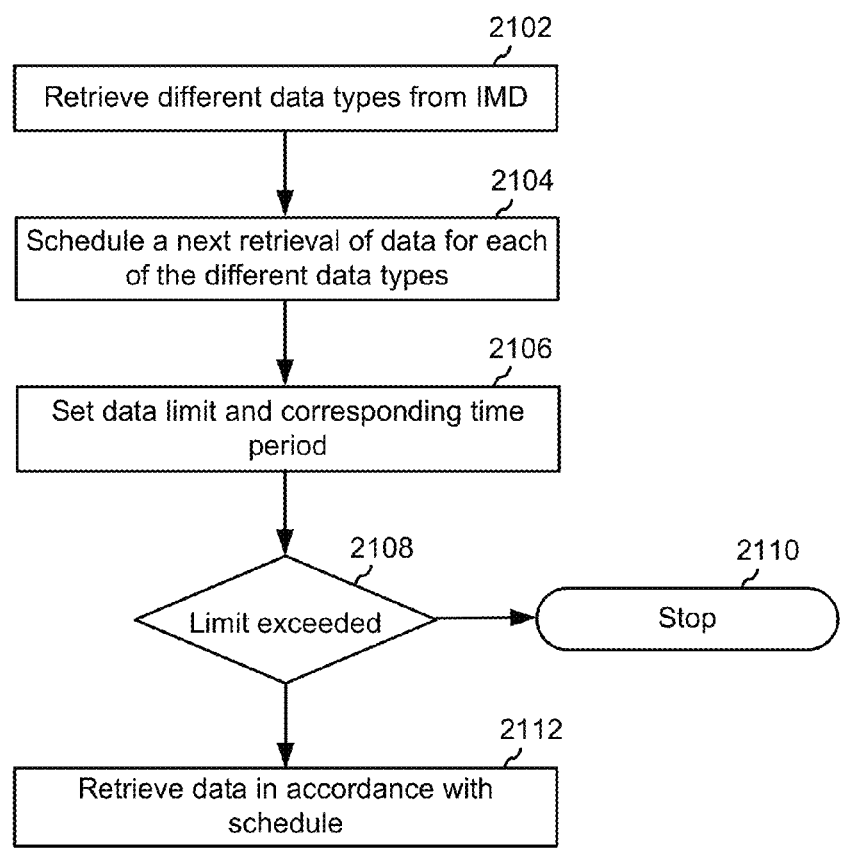
FIG. 21 is a flow chart of a method of scheduling data retrieval by a data retrieval apparatus.

With reference to FIG. 21, a process for scheduling the retrieval of data from an active implantable medical device is shown. The process may be performed by a data retrieval apparatus. The data retrieval apparatus retrieves different data types from an active implantable medical device (step 2102). Each data type may have portion of a memory of the implantable medical device allocated to it, such as described above with reference to FIG. 7. The data types may include different types of data, such as those also described with reference to FIG. 7. In summary, a first type may be histogram data collected over a known period of time that includes a count of a number of occurrences of at least one type of a physiological event over a period of time. A second type may be a time and order of occurrence of each of a number of different physiological events. The third type may be waveforms recordings of physiological events.

The data retrieval apparatus schedules a next retrieval of the data type (step 2104) based on a known period of time or based on time data included in retrieved data. For example, in the case of the first type of data, the data retrieval apparatus calculates a percentage of the period of time during which histogram data is collected and schedules the next retrieval of this data type as a percentage of that period of time. In the case of the second type of data, the data retrieval apparatus determines the elapsed time between the oldest occurrence of second data type and the most recent occurrence of second data type and schedules the next retrieval based on the elapsed time. For example, the data retrieval apparatus may set the time as a percentage of the elapsed time. In the case of the third data type, the data retrieval apparatus determines the elapsed time between the most recent data retrieval and the occurrence of the oldest waveform if all waveform allocations are used and schedules the next retrieval based on the elapsed time or a percentage thereof. Alternatively, if all waveform data memory is not used the next retrieval may be extended by a fixed or pro-rated amount based on actual memory usage.

The data retrieval apparatus may set a limit on the amount of data to be retrieved during a period of time (step 2106). A limit and time period may be separately set for each of the types of data stored in the implantable medical device. Prior to the next scheduled data retrieval, the data retrieval apparatus determines whether the limit on the data, or the type of data, for the current time period as been exceeded (step 2108). If the limit has been exceeded, the data retrieval apparatus stops and refrains from retrieving data (step 2110). If the limit on the data has not been exceeded, the data retrieval apparatus retrieves the data, or data type, in accordance with the schedule (step 2112).

Figure 22:
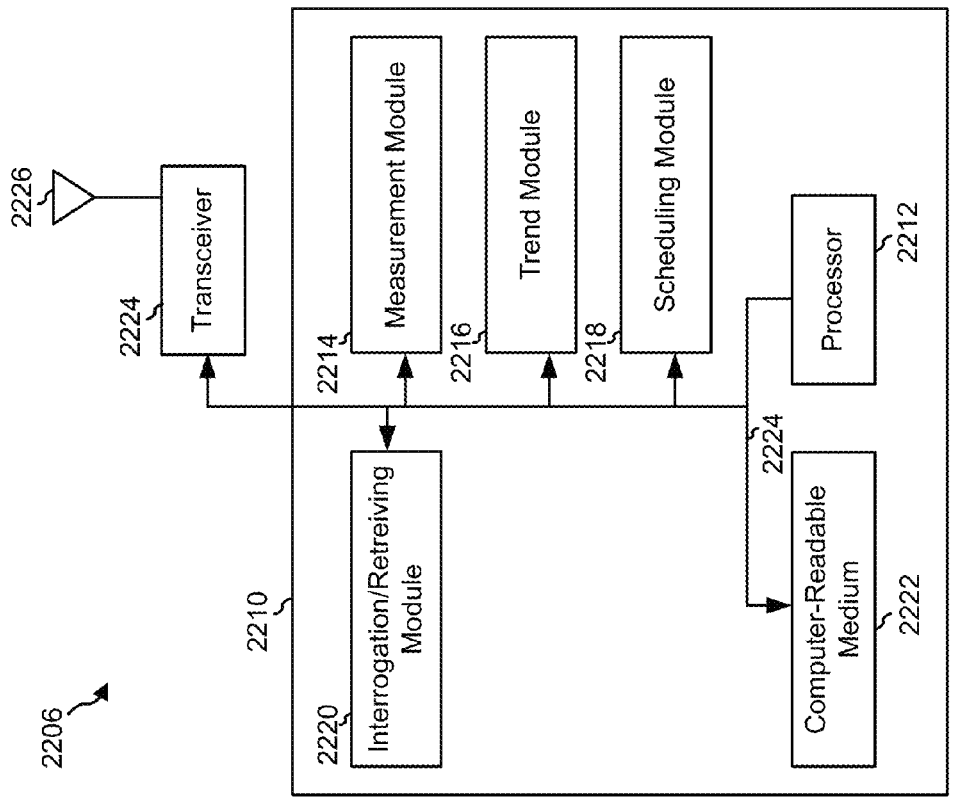
FIG. 22 is a diagram of an exemplary hardware implementation of a data retrieval apparatus.

FIG. 22 is a diagram illustrating an example of a hardware implementation for a data retrieval apparatus 2206 employing a processing system 2210. The processing system 2210 may be implemented with a bus architecture, represented generally by the bus 2224. The bus 2224 may include any number of interconnecting buses and bridges depending on the specific application of the processing system 2210 and the overall design constraints. The bus 2224 links together various circuits including one or more processors and/or hardware modules, represented by the processor 2212, a measurement module 2214, a trend module 2216, a scheduling module 2218, an interrogation/retrieving module 2220, and a computer-readable medium 2222. The bus 2224 may also link various other circuits such as timing sources, peripherals, voltage regulators, and power management circuits, which are well known in the art, and therefore, will not be described any further.

When functioning to implement the method of FIG. 17, the modules 2214, 2216, 2218 and 2220 function as follows: The measurement module 2214 obtains a plurality of measures over a period of time. The measures correspond to a quality of a communications channel between the data retrieval apparatus and an active implantable medical device. The trend module 2216 determines a trend in the plurality of measures over the period of time. The scheduling module 2218 determines a preferred time during which to retrieve data based on the trend. The interrogation/retrieving module 2220 interrogates the implantable medical device to retrieve data at or during the preferred time, and monitors for unsuccessful interrogation attempts. If a prerequisite number of interrogation attempts are unsuccessful, the modules 2214, 2216, 2218 and 2220 the obtain a new plurality of measures, determine another trend and preferred time, based on the new measures.

When functioning to implement the method of FIG. 21, the modules 2214, 2216, 2218 and 2220 function as follows: The interrogation/retrieving module 2220 retrieves different data types from an active implantable medical device. Each data type has a portion of a memory of the implantable medical device allocated to it. The scheduling module 2218 schedules a next retrieval of each of the data types based on a known period of time or based on time data included in retrieved data.

The modules 2214, 2216, 2218 and 2220 may be software modules running in the processor 2212, resident/stored in the computer readable medium 2222, one or more hardware modules coupled to the processor 2212, or some combination thereof. The processing system 2210 may be coupled to a transceiver 2224. The transceiver 2224 is coupled to one or more antennas 2226. The transceiver 2224 provides a means for communicating with various other apparatus over a transmission medium, including for example an implantable medical device. The transceiver 2224 receives a signal from the one or more antennas 2226, extracts information from the received signal, and provides the extracted information to the processing system 2210. In addition, the transceiver 2224 receives information from the processing system 2210 and based on the received information, generates a signal to be applied to the one or more antennas 2226.

The processing system 2210 includes a processor 2212 coupled to a computer-readable medium 2206. The processor 2212 is responsible for general processing, including the execution of software stored on the computer-readable medium 2222. The software, when executed by the processor 2212, causes the processing system 2210 to perform the various functions described supra for any particular module. The computer-readable medium 2222 may also be used for storing data that is manipulated by the processor 2212 when executing software.

Figure 23:
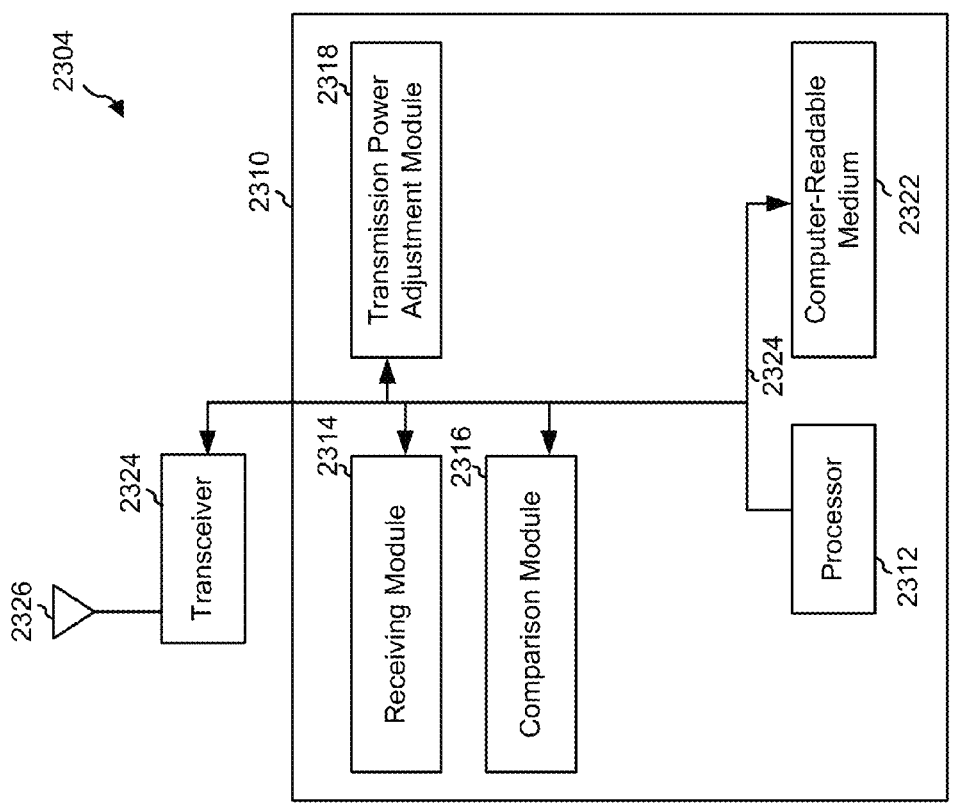
FIG. 23 is a diagram of an exemplary hardware implementation of an implantable medical device.

FIG. 23 is a diagram illustrating an example of a hardware implementation for an active implantable medical device 2304 employing a processing system 2310. The processing system 2310 may be implemented with a bus architecture, represented generally by the bus 2324. The bus 2324 may include any number of interconnecting buses and bridges depending on the specific application of the processing system 2310 and the overall design constraints. The bus 2324 links together various circuits including one or more processors and/or hardware modules, represented by the processor 2312, a receiving module 2314, a comparison module 2316, a transmission power adjustment module 2318, and a computer-readable medium 2322. The bus 2324 may also link various other circuits such as timing sources, peripherals, voltage regulators, and power management circuits, which are well known in the art, and therefore, will not be described any further.

When functioning to implement the method of FIG. 19, the modules 2314, 2316, and 2318 function as follows: The receiving module 2314 receives a measure of quality of a signal transmitted by the active implantable medical device. The measure is received from an external data retrieval apparatus that received the signal transmitted by the implantable medical device. The comparison module 2316 compares the quality measure to a minimum criterion. The criterion corresponds to a minimum quality measure, which in turn, corresponds to a minimum performance requirement for a communication channel between the implantable medical device and the data retrieval apparatus. The minimum performance requirement may be a data rate, and the measure of quality may be one of a signal-to-noise, a received signal strength indication, and a packet error rate. The transmission power adjustment module 2318 adjusts a signal transmission power level until the measure is at or near the criterion.

The modules 2314, 2316 and 2318 may be software modules running in the processor 2312, resident/stored in the computer readable medium 2322, one or more hardware modules coupled to the processor 2312, or some combination thereof. The processing system 2310 may be coupled to a transceiver 2324. The transceiver 2324 is coupled to one or more antennas 2326. The transceiver 2324 provides a means for communicating with various other apparatus over a transmission medium, including for example an implantable medical device. The transceiver 2324 receives a signal from the one or more antennas 2326, extracts information from the received signal, and provides the extracted information to the processing system 2310. In addition, the transceiver 2324 receives information from the processing system 2310 and based on the received information, generates a signal to be applied to the one or more antennas 2326.

The processing system 2310 includes a processor 2312 coupled to a computer-readable medium 2306. The processor 2312 is responsible for general processing, including the execution of software stored on the computer-readable medium 2322. The software, when executed by the processor 2312, causes the processing system 2310 to perform the various functions described supra for any particular module. The computer-readable medium 2322 may also be used for storing data that is manipulated by the processor 2312 when executing software.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method of power transmission control by an active implantable medical device, the method comprising:
　establishing a communications link with an external data retrieval apparatus during a portion of a period of time, wherein the portion corresponds to a time during which a measure of quality of a signal transmitted by the active implantable medical device and received by the external apparatus has previously satisfied a criterion value;
　transmitting data to the external data retrieval apparatus during the portion of the period of time; and
　controlling a signal transmission power level of the implantable medical device during the portion of the period of time by:
　　receiving a current measure of quality of a signal transmitted by the active implantable medical device, the current measure received from the external data retrieval apparatus;

comparing the current measure to the criterion value; and adjusting the signal transmission power level until the current measure is at or near the criterion value.

2. The method of claim 1, wherein the criterion value corresponds to a minimum quality measure, which in turn, corresponds to a minimum performance requirement for a communication channel between the active implantable medical device and the external data retrieval apparatus.

3. The method of claim 2, wherein the minimum performance requirement corresponds to a data rate.

4. The method of claim 1, wherein the period of time is 24 hours and the portion of the period of time is less than 24 hours.

5. The method of claim 1, wherein the measure of quality comprises a signal-to-noise ratio, the criterion value comprises a minimum signal-to-noise ratio, and the signal transmission power level is adjusted until the measure of quality is at or near the minimum signal-to-noise ratio.

6. The method of claim 1, wherein the measure of quality comprises a received signal strength indicator, the criterion value comprises a minimum signal strength indicator, and the signal transmission power level is adjusted until the measure of quality is at or near the minimum received signal strength indicator.

7. The method of claim 1, wherein the measure of quality comprises a packet error rate, the criterion value comprises a maximum packet error rate, and the signal transmission power level is adjusted until the measure of quality is at or near the maximum packet error rate.

8. The method of claim 1, wherein the time during which a measure of quality of a signal transmitted by the active implantable medical device and received by the external apparatus has previously satisfied a criterion value is determined based on a trend in a plurality of signal quality measures obtained over a plurality of previous periods of time.

9. An active implantable medical device, comprising:
a transceiver configured to:
establish a communications link with an external data retrieval apparatus during a portion of a period of time, wherein the portion corresponds to a time during which a measure of quality of a signal transmitted by the active implantable medical device and received by the external apparatus has previously satisfied a criterion value;
transmit data to the external data retrieval apparatus during the portion of the period of time; and a processing system coupled to the transceiver and configured to control a signal transmission power level of the implantable medical device during the portion of the period of time by being further configured to:
receive a current measure of quality of a signal transmitted by the active implantable medical device, the current measure received from the external data retrieval apparatus;
compare the current measure to the criterion value; and
adjust the signal transmission power level until the current measure is at or near the criterion value.

10. The active implantable medical device of claim 9, wherein the criterion value corresponds to a minimum quality measure, which in turn, corresponds to a minimum performance requirement for a communication channel between the active implantable medical device and the external data retrieval apparatus.

11. The active implantable medical device of claim 10, wherein the minimum performance requirement corresponds to a data rate.

12. The active implantable medical device of claim 9, wherein the period of time is 24 hours and the portion of the period of time is less than 24 hours.

13. The active implantable medical device of claim 9, wherein the measure of quality comprises a signal-to-noise ratio, the criterion value comprises a minimum signal-to-noise ratio, and the signal transmission power level is adjusted until the measure of quality is at or near the minimum signal-to-noise ratio.

14. The active implantable medical device of claim 9, wherein the measure of quality comprises a received signal strength indicator, the criterion value comprises a minimum signal strength indicator, and the signal transmission power level is adjusted until the measure of quality is at or near the minimum received signal strength indicator.

15. The active implantable medical device of claim 9, wherein the measure of quality comprises a packet error rate, the criterion value comprises a maximum packet error rate, and the signal transmission power level is adjusted until the measure of quality is at or near the maximum packet error rate.

16. The active implantable medical device of claim 9, wherein the time during which a measure of quality of a signal transmitted by the active implantable medical device and received by the external apparatus has previously satisfied a criterion value is determined based on a trend in a plurality of signal quality measures obtained over a plurality of previous periods of time.

* * * * *